United States Patent
Tateishi et al.

(10) Patent No.: US 8,399,664 B2
(45) Date of Patent: *Mar. 19, 2013

(54) COLORING MATTER, INK, INK FOR INK JET, INK JET RECORDING METHOD, COLOR TONER, AND COLOR FILTER

(75) Inventors: Keiichi Tateishi, Kanagawa (JP); Yoshiharu Yabuki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/329,466

(22) Filed: Dec. 19, 2011

(65) Prior Publication Data

US 2012/0088910 A1    Apr. 12, 2012

Related U.S. Application Data

(62) Division of application No. 11/795,581, filed as application No. PCT/JP2005/014439 on Aug. 5, 2005, now Pat. No. 8,101,011.

(30) Foreign Application Priority Data

Feb. 7, 2005  (JP) ................... 2005-030466
Aug. 4, 2005  (JP) ................... 2005-226768

(51) Int. Cl.
  C07D 403/14   (2006.01)
  C07D 251/52   (2006.01)
  A61K 31/53    (2006.01)
  C09D 11/02    (2006.01)
  C09B 31/143   (2006.01)

(52) U.S. Cl. ............ 544/209; 106/31.46; 106/31.48; 106/31.5; 534/755; 534/758; 534/769

(58) Field of Classification Search .......... 544/209
See application file for complete search history.

(56) References Cited

U.S. PATENT DOCUMENTS

| | | | |
|---|---|---|---|
| 4,685,934 A | 8/1987 | Benguerel et al. | |
| 4,737,190 A | 4/1988 | Shimada et al. | |
| 6,231,653 B1 | 5/2001 | Lavery et al. | |
| 6,331,204 B1 | 12/2001 | Carr et al. | |
| 6,878,196 B2 | 4/2005 | Harada et al. | |
| 7,022,170 B2 | 4/2006 | Taguchi et al. | |
| 7,125,446 B2 | 10/2006 | Potenza et al. | |
| 7,507,282 B2 | 3/2009 | Ozawa et al. | |
| 7,510,605 B2 | 3/2009 | Harada et al. | |
| 8,101,011 B2* | 1/2012 | Tateishi et al. | 106/31.46 |
| 2003/0213405 A1 | 11/2003 | Harada et al. | |
| 2004/0066438 A1 | 4/2004 | Taguchi et al. | |
| 2006/0016368 A1 | 1/2006 | Ozawa et al. | |
| 2010/0302305 A1 | 12/2010 | Tateishi et al. | |

FOREIGN PATENT DOCUMENTS

| | | |
|---|---|---|
| DE | 25 39 653 A1 | 4/1976 |
| EP | 0 331 170 A2 | 9/1989 |
| EP | 1 357 158 A1 | 4/2003 |
| EP | 1380623 A1 | 1/2004 |
| EP | 1403337 A1 | 3/2004 |
| EP | 1 619 224 A1 | 1/2006 |
| JP | 58-057478 A | 4/1983 |
| JP | 61-101574 A | 5/1986 |
| JP | 6-25575 A | 2/1994 |
| JP | 6-228476 A | 8/1994 |
| JP | 6-248212 A | 9/1994 |
| JP | 7-26178 A | 1/1995 |
| JP | 7-228810 A | 8/1995 |
| JP | 7-268261 A | 10/1995 |
| JP | 8-259865 A | 10/1996 |
| JP | 8-337745 A | 12/1996 |
| JP | 9-012946 A | 1/1997 |
| JP | 9-012949 A | 1/1997 |
| JP | 10-279858 A | 10/1998 |
| JP | 10-329418 A | 12/1998 |
| JP | 2000-085236 A | 3/2000 |
| JP | 2002-146249 A | 5/2002 |

(Continued)

OTHER PUBLICATIONS

Extended European Search Report for Application No. 05768616.4 dated Aug. 22, 2008.
Extended European Search Report for Application No. 09180583.8 dated Feb. 15, 2010.
Japanese Notification of Reasons for Refusal, dated Mar. 8, 2011, issued in Application No. 2005-151254.

*Primary Examiner* — Venkataraman Balasubramanian
(74) *Attorney, Agent, or Firm* — Sughrue Mion, PLLC

(57) ABSTRACT

[Problem] To provide a coloring matter which has a good hue, and is capable of forming an image high in fastness property under various use conditions and environmental conditions, and particularly suitable for an ink.
[Solving Means] A coloring matter represented by the following formula (I):

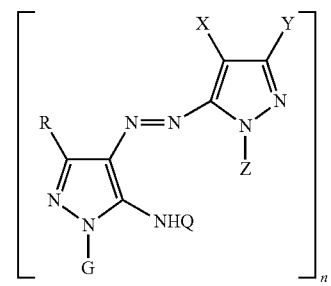

wherein in the formula, G represents a heterocyclic group, and n represents an integer of 1 to 3; when n is 1, R, X, Y, Z, Q, and G each represents a monovalent group; when n is 2, R, X, Y, Z, Q, and G each represents a monovalent or divalent substituent, provided that at least one represents a divalent substituent; and when n is 3, R, X, Y, Z, Q, and G each represents a monovalent, divalent or trivalent substituent, provided that at least two each represents a divalent substituent, or at least one represents a trivalent substituent.

2 Claims, No Drawings

| | FOREIGN PATENT DOCUMENTS | | |
|---|---|---|---|
| JP | 2003-277662 A | 2/2003 | |
| JP | 2003-238862 A | 8/2003 | |
| JP | 2003-277661 A | 10/2003 | |
| JP | 2004-001265 A | 1/2004 | |
| JP | 2004-091537 A | 3/2004 | |
| JP | 2004-149612 A | 5/2004 | |
| JP | 2004-149613 A | 5/2004 | |
| JP | 2004-182977 A | 7/2004 | |
| JP | 2007-063520 A | 3/2007 | |
| WO | WO 95/34024 A1 | 2/1995 | |
| WO | WO 2004/018574 A1 | 3/2004 | |
| WO | WO 2005/075573 A1 | 8/2005 | |
| WO | WO 2006-055466 A1 | 5/2006 | |

\* cited by examiner

COLORING MATTER, INK, INK FOR INK JET, INK JET RECORDING METHOD, COLOR TONER, AND COLOR FILTER

This application is a divisional of U.S. patent application Ser. No. 11/795,581 filed Jul. 19, 2007, which is a national stage of PCT Application No. PCT/JP2005/014439 filed Aug. 5, 2005, which claims benefit to Japanese Patent Application No. 2005-030466 filed Feb. 7, 2005, and Japanese Patent Application No. 2005-226768 filed Aug. 4, 2005. The above-noted applications are incorporated herein by reference in their entirety.

TECHNICAL FIELD

The present invention relates to an ink, an ink for ink jet, an ink jet recording method, a method for improving the weatherability of a formed colored image material, an ink sheet, a color toner, and a color filter.

BACKGROUND ART

In recent years, as image recording materials, particularly, materials for forming color images have been mainstream. Specifically, recording materials of an ink jet system, recording materials of a heat sensitive transfer system, recording materials of an electrophotographic system, transfer type silver halide light sensitive materials, printing inks, recording pens, and the like have found widespread use. Whereas, in image pickup devices such as CCDs for photographing equipment, and in LCDs and PDPs for displays, color filters are used for recording/reproducing color images. For these color image recording materials and color filters, coloring matters (dyes and pigments) of three primary colors of a so-called additive color mixing process or subtractive color mixing process have been used in order to display or record full-color images. However, in actuality, there is no fast coloring matter having the absorption characteristics capable of realizing a preferred color reproduction region, and resisting various use conditions and environmental conditions. Thus, the improvement thereof has been strongly desired.

The coloring matters for use in the respective applications are required to have in common the following properties. Namely, the absorption characteristics in terms of color reproduction are preferable; fastness properties under the environmental conditions in which they are used, such as the light resistance, heat resistance, moisture resistance, the resistance to an oxidizing gas such as ozone, fastness properties to chemicals such as sulfurous acid gas are good; the storage stability in an ink is excellent; and other properties. There is a strong demand for a coloring matter which has a good yellow hue, is fast to light, moist heat, and active gases in the environment, and is excellent in storage stability.

As the coloring matter skeleton of yellow for use as an ink for ink jet, azo type one is typical. As the typical azo coloring matter, in JP-A-2003-277662, there is described a fast coloring matter having a triazinyl pyrazole skeleton. However, there is further a demand for a coloring matter excellent in storage stability in an ink.

Patent Document 1: JP-A-2003-277662

DISCLOSURE OF THE INVENTION

Problems that the Invention is to Solve

It is objects of the present invention to resolve the problems in the related art, and to attain the following objects.

Namely, the objects of the invention are 1) to provide a coloring matter which has the absorption characteristics of excellent color reproduction as the coloring matter of three primary colors, has sufficient fastness properties to light, heat, moisture, and active gases in the environment, and excellent in the storage stability in an ink; 2) to provide various coloring compositions (inks) for an ink for ink jet printing or other printing, an ink sheet in a heat sensitive recording material, a color toner for electrophotography, and a color filter for use in a display such as LCD or PDP, or an image pick-up device such as CCD, for providing a colored image or a colored material excellent in hue and fastness properties, and 3) to provide, particularly, an ink for ink jet recording which is excellent in storage stability in an ink, has a good hue, and is capable of forming an image high in fastness properties to light, moist heat, and active gases in the environment, particularly, an ozone gas, and an ink jet recording method.

Means for Solving the Problems

The present inventors conducted a close study on a pyrazolyl azo coloring matter derivative aiming at a coloring matter excellent in ink stability, having a good hue, and high in fastness properties to light, ozone, and moist heat. As a result, they found that the problems can be solved by the compounds represented by the following formulae (I), and (1) to (6), leading to the completion of the invention. The means for solving the problems are as follows.

<1> A coloring matter represented by the following formula (I):

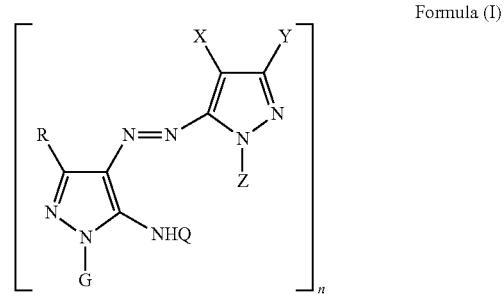

Formula (I)

wherein in the formula, G represents a heterocyclic group, and n represents an integer of 1 to 3; when n is 1, R, X, Y, Z, Q, and G each represents a monovalent group; when n is 2, R, X, Y, Z, Q, and G each represents a monovalent or divalent substituent, provided that at least one represents a divalent substituent; and when n is 3, R, X, Y, Z, Q, and G each represents a monovalent, divalent, or trivalent substituent, provided that at least two each represents a divalent substituent, or at least one represents a trivalent substituent.

<2> The coloring matter represented by the following formula (1), formula (2), formula (3), formula (4), or formula (5):

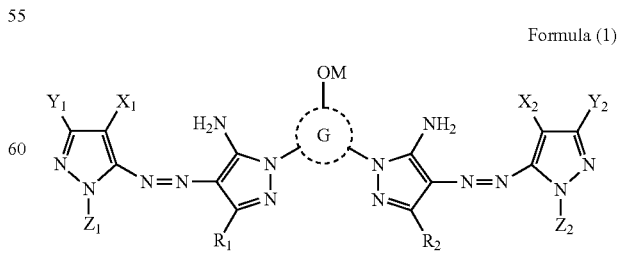

Formula (1)

wherein in the formula, $R_1$, $R_2$, $X_1$, $X_2$, $Y_1$, $Y_2$, $Z_1$, and $Z_2$ each represents a monovalent group, G represents an atomic group forming a 5- to 8-membered nitrogen-containing heterocyclic ring, and M represents a hydrogen atom or a cation;

Formula (2)

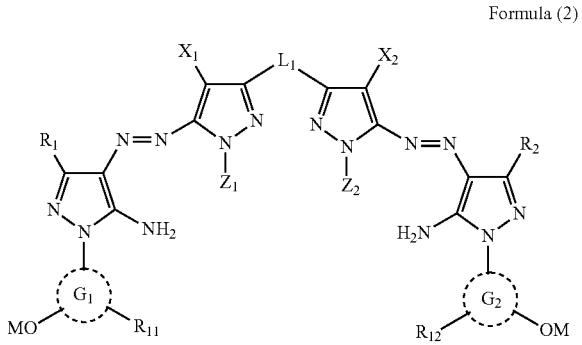

wherein in the formula, $R_1$, $R_2$, $R_{11}$, $R_{12}$, $X_1$, $X_2$, $Z_1$, and $Z_2$ each represents a monovalent group, $L_1$ represents a divalent linking group, $G_1$ and $G_2$ each independently represents an atomic group forming a 5- to 8-membered nitrogen-containing heterocyclic ring, and M represents a hydrogen atom or a cation;

Formula (3)

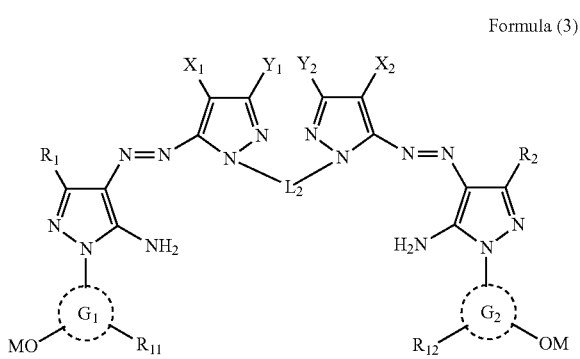

wherein in the formula, $R_1$, $R_2$, $R_{11}$, $R_{12}$, $X_1$, $X_2$, $Y_1$, and $Y_2$ each represents a monovalent group, $L_2$ represents a divalent linking group, $G_1$ and $G_2$ each independently represents an atomic group forming a 5- to 8-membered nitrogen-containing heterocyclic ring, and M represents a hydrogen atom or a cation;

Formula (4)

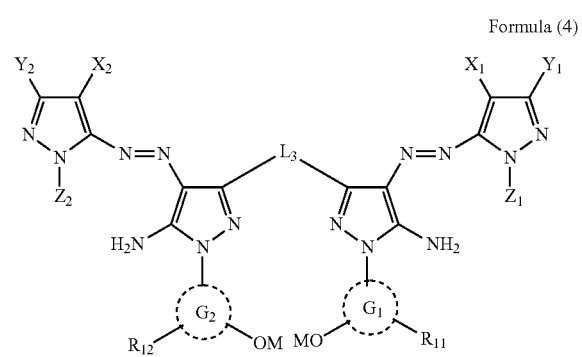

wherein in the formula, $R_{11}$, $R_{12}$, $X_1$, $X_2$, $Y_1$, $Y_2$, $Z_1$, and $Z_2$ each represents a monovalent group, $L_3$ represents a divalent linking group, $G_1$ and $G_2$ each independently represents an atomic group forming a 5- to 8-membered nitrogen-containing heterocyclic ring, and M represents a hydrogen atom or a cation; and Formula (5)

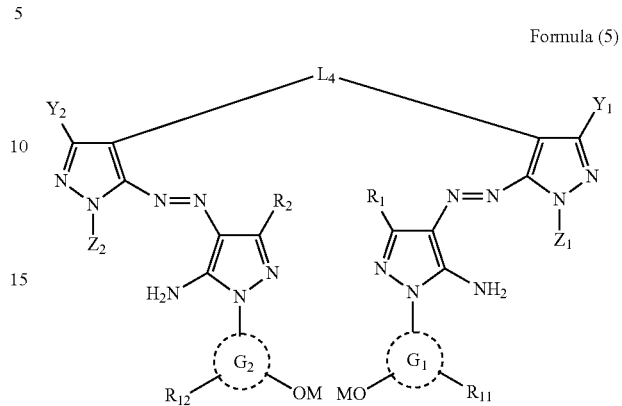

wherein in the formula, $R_1$, $R_2$, $R_{11}$, $R_{12}$, $Y_1$, $Y_2$, $Z_1$, and $Z_2$ each represents a monovalent group, $L_4$ represents a divalent linking group, $G_1$ and $G_2$ each independently represents an atomic group forming a 5- to 8-membered nitrogen-containing heterocyclic ring, and M represents a hydrogen atom or a cation.

<3> The coloring matter according to the item <2>, wherein each nitrogen-containing heterocyclic ring represented by G, $G_1$, and $G_2$ in the formula (1), the formula (2), the formula (3), the formula (4), and the formula (5) is a S-triazine ring.

<4> The coloring matter according to the item <2>, wherein the coloring matter represented by the formula (1) is a coloring matter represented by the following formula (6):

Formula (6)

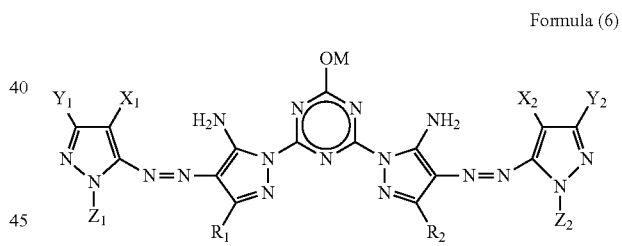

where in the formula, $R_1$, $R_2$, $Y_1$, and $Y_2$ each represents a monovalent group; $X_1$ and $X_2$ each independently represents an electron attracting group with a Hammett's σp value of 0.20 or more; $Z_1$ and $Z_2$ each independently represents a hydrogen atom, a substituted or unsubstituted alkyl group, a substituted or unsubstituted alkenyl group, a substituted or unsubstituted alkynyl group, a substituted or unsubstituted aralkyl group, a substituted or unsubstituted aryl group, or a substituted or unsubstituted heterocyclic group; and M represents a hydrogen atom or a cation.

<5> An ink comprising at least one coloring matter according to any of the items <1> to <4>.

<6> An ink for ink jet recording which uses an ink according to the item <5>.

<7> An ink jet recording method for image formation using an ink according to the item <6>.

<8> An ink jet recording method comprising:
forming an image on an image receiving material having an ink image receiving layer containing white inorganic pigment particles on a support using an ink according to the item <6>.

<9> A method for improving weatherability of a colored image material formed by using an ink according to the item <6>.

<10> An ink sheet comprising at least one coloring matter according to any of the items <1> to <4>.

<11> A color toner comprising at least one coloring matter according to any of the items <1> to <4>.

<12> A color filter comprising at least one coloring matter according to any of the items <1> to <4>.

<13> A compound represented by the following formula (7), or a salt or a hydrate thereof:

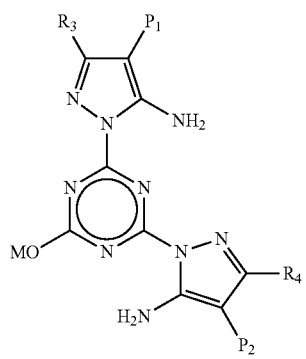

Formula (7)

wherein in the formula, $R_3$ and $R_4$ each independently represents a monovalent group; $P_1$ and $P_2$ each independently represents a hydrogen atom or a leaving group; and M represents a hydrogen atom or a cation.

Advantage of the Invention

The coloring matter of the present invention is excellent in storage stability in an ink. It has the absorption characteristics of excellent color reproduction as the coloring matter of three primary colors, and has sufficient fastness properties to light, heat, moisture, and active gases in the environment. Further, the coloring matter is suitable as for various coloring compositions of an ink for ink jet printing or other printing, an ink sheet in a heat sensitive recording material, a color toner for electrophotography, and a color filter for use in a display such as LCD or PDP, or an image pick-up device such as CCD, for providing a colored image or a colored material excellent in hue and fastness properties. Particularly, use of the coloring matter can provide an ink for ink jet recording which is excellent in storage stability in an ink, has a good hue, and is capable of forming an image high in fastness properties to light, and active gases in the environment, particularly, an ozone gas, and an ink jet recording method.

BEST MODE FOR CARRYING OUT THE INVENTION

Below, the present invention will be described in details.

[Azo Coloring Matter]

Herein, the Hammett's substituent constant σup value used in this specification will be explained to some extent. The Hammett's rule is an empirical rule proposed by L. P. Hammett in 1935 in order to discuss quantitatively the effect of a substituent on the reaction or equilibrium of benzene derivatives. The propriety of the rule is widely recognized at present. The substituent constants determined by the Hammett's rule include the σp value and the σm value. These values can be found widely in common literature. For example, these are specifically described in Lange's Handbook of Chemistry, 12th Edition, compiled by J. A. Dean, 1979, (McGraw Hill), and Kagaku No Ryouiki, a special issue, No. 122, pp. 96 to 103, 1979, (Nankoudo). Incidentally, although in the invention, respective substituents are defined by the Hammett's substituent constant σp value, or described thereby, this should not be construed as limitation to only substituents whose values are known by literature and can be found in the above publications, and should naturally be construed as including substituents whose values, even if unknown by literature, would be included in the ranges when measured according to the Hammett's rule. Although the compounds represented by the formula (B) of the invention are not benzene derivatives, the σp value is used, irrespective of substitution site, as a scale for showing the electronic effect of substituents thereof. In the invention, the σp value will be hereinafter used in such a meaning.

The azo coloring matters in the invention are the azo coloring matters represented by the formulae (1) to (6).

Below, the formula (I) will be described in details.

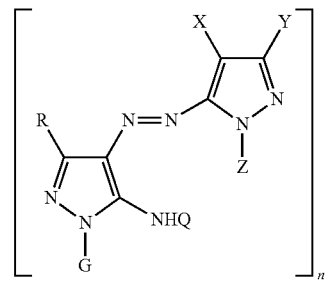

where in the formula, G represents a heterocyclic group, and n represents an integer of 1 to 3.

When n is 1, R, X, Y, Z, Q, and G each represent a monovalent group, and represent a monoazo coloring matter represented by the formula in the parentheses.

When n is 2, R, X, Y, Z, Q, and G each represent a monovalent or divalent group, provided that at least one represents a divalent substituent, and represent a bis type azo coloring matter of the coloring matter represented by the formula in the parentheses.

When n is 3, R, X, Y, Z, Q, and G each represent a divalent or trivalent group, provided that at least two each represent a divalent substituent, or at least one represents a trivalent substituent, and represent a tris type azo coloring matter of the coloring matter represented by the formula in the parentheses.

Below, the formula (I) will be further described in details.

In the formula (I), preferred examples of the substituent of G include preferably 5- to 8-membered heterocyclic groups. Out of these, 5- to 8-membered substituted or unsubstituted, aromatic or nonaromatic heterocyclic groups are preferred. They may be further condensed. A 5- or 6-membered aromatic heterocyclic group having 3 to 30 carbon atoms is further preferred.

Examples of the heterocyclic group represented by the G may include, with no limitation on substitution site, pyridine, pyrazine, pyridazine, pyrimidine, triazine, quinoline, isoquinoline, quinazoline, cinnoline, phthalazine, quinoxaline, pyrrole, indole, furan, benzofuran, thiophene, benzothiophene, pyrazole, imidazole, benzimidazole, triazole, oxazole, benzoxazole, thiazole, benzothiazole, isothiazole, benzisothiazole, thiadiazole, isoxazole, benzisoxazole, pyrrolidine, piperidine, piperazine, imidazolidine, and thiazoline.

When the heterocyclic group is a group capable of further having a substituent, it may further have the following substituents.

Mention may be made of a straight chain or branched alkyl group having 1 to 12 carbon atoms, a straight chain or branched aralkyl group having 7 to 18 carbon atoms, a straight chain or branched alkenyl group having 2 to 12 carbon atoms, a straight chain or branched alkynyl group having 2 to 12 carbon atoms, a straight chain or branched cycloalkyl group having 3 to 12 carbon atoms, a straight-chain or branched cycloalkenyl group having 3 to 12 carbon atoms (out of the foregoing respective groups, those having branched chains are preferable because they improve the solubility of the dye and the stability of the ink; and those having asymmetric carbons are particularly preferred; examples of which include methyl, ethyl, propyl, isopropyl, sec-butyl, t-butyl, 2-ethylhexyl, 2-methyl sulfonyl ethyl, 3-phenoxypropyl, trifluoromethyl, and cyclopentyl), a halogen atom (e.g., a chlorine atom or a bromine atom), an aryl group (e.g., phenyl, 4-t-butylphenyl, or 2,4-di-t-amyl phenyl), a heterocyclic group (e.g., imidazolyl, pyrazolyl, thoriazolyl, 2-furyl, 2-thienyl, 2-pyrimidinyl, or 2-benzothiazolyl), a cyano group, a hydroxyl group, a nitro group, a carboxy group, an amino group, an alkyloxy group (e.g., methoxy, ethoxy, 2-methoxyethoxy, or 2-methyl sulfonyl ethoxy), an aryloxy group (e.g., a phenoxy, 2-methyl phenoxy, 4-t-butyl phenoxy, 3-nitro phenoxy, 3-t-butyloxy carbonyl phenoxy, or 3-methoxy carbonylphenyloxy), or an acylamino group (e.g., acetamide, benzamide, or 4-(3-t-butyl-4-hydroxy phenoxy) butane amide), an alkylamino group (e.g., methylamino, butylamino, diethylamino, or methyl butylamino), an anilino group (e.g., phenyl amino or 2-chloroanilino), an ureido group (e.g., phenylureido, methylureido, or N,N-dibutylureido), a sulfamoyl amino group (e.g., N,N-dipropyl sulfamoyl amino), an alkyl thio group (e.g., methyl thio, octyl thio, 2-phenoxyethyl thio), an aryl thio group (e.g., phenyl thio, 2-butoxy-5-t-octylphenyl thio, or 2-carboxy phenyl thio), an alkyloxy carbonyl amino group (e.g., methoxy carbonyl amino), an alkyl sulfonyl amino group, and an aryl sulfonyl amino group (e.g., methyl sulfonyl amino, phenyl sulfonyl amino, or p-toluene sulfonyl amino), a carbamoyl group (e.g., N-ethyl carbamoyl or N,N-dibutyl carbamoyl), a sulfamoyl group (e.g., N-ethyl sulfamoyl, N,N-dipropyl sulfamoyl, or N-phenyl sulfamoyl), a sulfonyl group (e.g., methyl sulfonyl, octyl sulfonyl, phenyl sulfonyl, or p-toluene sulfonyl), an alkyloxy carbonyl group (e.g., methoxy carbonyl or butyloxy carbonyl), a heterocyclic oxy group (e.g., 1-phenyltetrazol-5-oxy, 2-tetrahydropyranyloxy), an azo group (e.g., phenylazo, 4-methoxyphenyl azo, 4-pivaloylamino phenylazo, 2-hydroxy-4-propanoyl phenylazo), an acyloxy group (e.g., acetoxy), a carbamoyloxy group (e.g., N-methyl carbamoyloxy or N-phenylcarbamoyloxy), a silyloxy group (e.g., trimethyl silyloxy or dibutyl methyl silyloxy), an aryloxy carbonyl amino group (e.g., phenoxy carbonyl amino), an imido group (e.g., N-succinimido or N-phthalimido), a heterocyclic thio group (e.g., 2-benzothiazolyl thio, 2,4-di-phenoxy-1,3, 5-triazole-6-thio, 2-pyridylthio), a sulfinyl group (e.g., 3-phenoxypropyl sulfinyl), a phosphonyl group (e.g., phenoxy phosphonyl, octyloxy phosphonyl, or phenyl phosphonyl), an aryloxy carbonyl group (e.g., phenoxy carbonyl), an acyl group (e.g., acetyl, 3-phenyl propanoyl, or benzoyl), and ionic hydrophilic groups (e.g., a carboxyl group, a sulfo group, phosphono group, and a quaternary ammonium group).

Preferred examples of the substituents of Q, R, X, Y, and Z in the formula (I) will be described in details.

When Q, R, X, Y, and Z each represent a monovalent group, they each represent a hydrogen atom or a monovalent substituent as a monovalent group. The monovalent substituent will be described in more details. Examples of the monovalent substituent may include a halogen atom, an alkyl group, a cycloalkyl group, an aralkyl group, an alkenyl group, an alkynyl group, an aryl group, a heterocyclic group, a cyano group, a hydroxyl group, a nitro group, an alkoxy group, an aryloxy group, a silyloxy group, a heterocyclic oxy group, an acyloxy group, a carbamoyloxy group, an alkoxy carbonyloxy group, an aryloxy carbonyloxy group, an amino group (an alkylamino group or an arylamino group), an acylamino group (amido group), an amino carbonyl amino group (an ureido group), an alkoxy carbonyl amino group, an aryloxy carbonyl amino group, a sulfamoyl amino group, an alkyl sulfonyl amino group, an aryl sulfonyl amino group, an alkyl thio group, an aryl thio group, a heterocyclic thio group, a sulfamoyl group, an alkyl sulfinyl group, an aryl sulfinyl group, an alkyl sulfonyl group, an aryl sulfonyl group, an acyl group, an aryloxy carbonyl group, an alkoxy carbonyl group, a carbamoyl group, a phosphino group, a phosphinyl group, a phosphinyloxy group, a phosphinyl amino group, a silyl group, an azo group, or an imido group. Each may further have a substituent.

Out of these, particularly preferred is a hydrogen atom, a halogen atom, an alkyl group, an aryl group, a heterocyclic group, a cyano group, an alkoxy group, an amido group, an ureido group, an alkyl sulfonyl amino group, an aryl sulfonyl amino group, a sulfamoyl group, an alkyl sulfonyl group, an aryl sulfonyl group, a carbamoyl group, or an alkoxy carbonyl group. Particularly, a hydrogen atom, a halogen atom, an alkyl group, an aryl group, a cyano group, an alkyl sulfonyl group, an aryl sulfonyl group, or a heterocyclic group is preferred. A hydrogen atom, an alkyl group, an aryl group, a cyano group, or an alkyl sulfonyl group is most preferred.

Below, the Q, R, X, Y, and Z will be further described in more details.

The halogen atoms represented by Q, R, X, Y, and Z each represent a chlorine atom, a bromine atom, or an iodine atom. Out of these, a chlorine atom or a bromine atom is preferred. Particularly, a chlorine atom is preferred.

The alkyl groups represented by Q, R, X, Y, and Z include a substituted or unsubstituted alkyl group. The substituted or unsubstituted alkyl group is preferably an alkyl group having 1 to 30 carbon atoms. As the examples of the substituent, mention may be made of the same ones as the substituents as mentioned when the G is a group capable of further having a substituent. Out of these, a hydroxy group, an alkoxy group, a cyano group, and a halogen atom, a sulfo group (which may also be in the form of a salt) or a carboxyl group (which may also be in the form of a salt) is preferred. Examples of the alkyl group may include methyl, ethyl, butyl, t-butyl, n-octyl, eicosyl, 2-chloroethyl, hydroxyethyl, cyano ethyl, or 4-sulfobutyl.

The cycloalkyl groups represented by Q, R, X, Y, and Z include a substituted or unsubstituted cycloalkyl group. The substituted or unsubstituted cycloalkyl group is preferably a cycloalkyl group having 5 to 30 carbon atoms. As the examples of the substituent, mention may be made of the same ones as the substituents as mentioned when the G is a group capable of further having a substituent. Examples of the cycloalkyl group may include cyclohexyl, cyclopentyl, or 4-n-dodecyl cyclohexyl.

The aralkyl groups represented by Q, R, X, Y, and Z include a substituted or unsubstituted aralkyl group. The substituted or unsubstituted aralkyl group is preferably an aralkyl group having 7 to 30 carbon atoms. As the examples of the substituent, mention may be made of the same ones as the substituents as mentioned when the G is a group capable of further having a substituent. Examples of the aralkyl may include benzyl and 2-phenethyl.

The alkenyl groups represented by Q, R, X, Y, and Z include a straight-chain, branched, or cyclic substituted or unsubstituted alkenyl group. It is preferably a substituted or unsubstituted alkenyl group having 2 to 30 carbon atoms, examples of which may include vinyl, allyl, prenyl, geranyl, oleyl, 2-cyclopenten-1-yl, and 2-cyclohexen-1-yl.

The alkynyl groups represented by Q, R, X, Y, and Z are each a substituted or unsubstituted alkynyl group having 2 to 30 carbon atoms. Examples thereof may include ethynyl or propargyl.

The aryl groups represented by Q, R, X, Y, and Z are each a substituted or unsubstituted aryl group having 6 to 30 carbon atoms. Examples thereof may include phenyl, p-tolyl, naphthyl, m-chlorophenyl, or o-hexadecanoyl aminophenyl. As the examples of the substituent, mention may be made of the same ones as the substituents as mentioned when the G is a group capable of further having a substituent.

The heterocyclic groups represented by Q, R, X, Y, and Z are each a monovalent group obtained by removing one hydrogen atoms from a 5- or 6-membered substituted or unsubstituted, aromatic or nonaromatic heterocyclic compound, which may also be further condensed. It is further preferably a 5- or 6-membered aromatic heterocyclic group having 3 to 30 carbon atoms. As the examples of the substituent, mention may be made of the same ones as the substituents as mentioned when the G is a group capable of further having a substituent. Examples of the heterocyclic group may include, with no limitation on substitution site, pyridine, pyrazine, pyridazine, pyrimidine, triazine, quinoline, isoquinoline, quinazoline, cinnoline, phthalazine, quinoxaline, pyrrole, indole, furan, benzofuran, thiophene, benzothiophene, pyrazole, imidazole, benzimidazole, triazole, oxazole, benzoxazole, thiazole, benzothiazole, isothiazole, benzisothiazole, thiadiazole, isoxazole, benzisoxazole, pyrrolidine, piperidine, piperazine, imidazolidine, and thiazoline.

The alkoxy groups represented by Q, R, X, Y, and Z each include a substituted or unsubstituted alkoxy group. The substituted or unsubstituted alkoxy group is preferably an alkoxy group having 1 to 30 carbon atoms. As the examples of the substituent, mention may be made of the same ones as the substituents as mentioned when the G is a group capable of further having a substituent. Examples of the alkoxy group may include methoxy, ethoxy, isopropoxy, n-octyloxy, methoxyethoxy, hydroxyethoxy, and 3-carboxy propoxy.

The aryloxy groups represented by Q, R, X, Y, and Z are each preferably a substituted or unsubstituted aryloxy group having 6 to 30 carbon atoms. As the examples of the substituent, mention may be made of the same ones as the substituents as mentioned when the G is a group capable of further having a substituent. Examples of the aryloxy group may include phenoxy, 2-methyl phenoxy, 4-t-butyl phenoxy, 3-nitro phenoxy, and 2-tetradecanoyl amino phenoxy.

The silyloxy groups represented by Q, R, X, Y, and Z are each preferably a silyloxy group having 3 to 20 carbon atoms. Examples thereof may include trimethyl silyloxy and t-butyldimethyl silyloxy.

The heterocyclic oxy groups represented by Q, R, X, Y, and Z are each preferably a substituted or unsubstituted heterocyclic oxy group having 2 to 30 carbon atoms. As the examples of the substituent, mention may be made of the same ones as the substituents as mentioned when the G is a group capable of further having a substituent. Examples of the heterocyclic oxy group may include, for example, 1-phenyltetrazol-5-oxy, and 2-tetrahydorpyranyloxy.

The acyloxy groups represented by Q, R, X, Y, and Z are each preferably a formyloxy group, a substituted or unsubstituted alkyl carbonyloxy group having 2 to 30 carbon atoms, or a substituted or unsubstituted aryl carbonyloxy group having 6 to 30 carbon atoms. As the examples of the substituent, mention may be made of the same ones as the substituents as mentioned when the G is a group capable of further having a substituent. Examples of the acyloxy group may include, for example, formyloxy, acetyloxy, pivaloyloxy, steaaroyloxy, benzoyloxy, and p-methoxyphenyl carbonyloxy.

The carbamoyloxy groups represented by Q, R, X, Y, and Z are each preferably a substituted or unsubstituted carbamoyloxy group having 1 to 30 carbon atoms. As the examples of the substituent, mention may be made of the same ones as the substituents as mentioned when the G is a group capable of further having a substituent. Examples of the carbamoyloxy group may include, for example, N,N-dimethyl carbamoyloxy, N,N-diethyl carbamoyloxy, morpholino carbonyloxy, and N,N-di-n-octyl amino carbonyloxy, N-n-octyl carbamoyloxy.

The alkoxy carbonyloxy groups represented by Q, R, X, Y, and Z are each preferably a substituted or unsubstituted alkoxy carbonyloxy group having 2 to 30 carbon atoms. As the examples of the substituent, mention may be made of the same ones as the substituents as mentioned when the G is a group capable of further having a substituent. Examples of the alkoxy carbonyloxy group may include, for example, methoxy carbonyloxy, ethoxy carbonyloxy, t-butoxy carbonyloxy, and n-octyl carbonyloxy.

The aryloxy carbonyloxy groups represented by Q, R, X, Y, and Z are each preferably a substituted or unsubstituted aryloxy carbonyloxy group having 7 to 30 carbon atoms. As the examples of the substituent, mention may be made of the same ones as the substituents as mentioned when the G is a group capable of further having a substituent. Examples of the aryloxy carbonyloxy group may include, for example, phenoxy carbonyloxy, p-methoxyphenoxy carbonyloxy, and p-n-hexadecyloxy phenoxy carbonyloxy.

The amino groups represented by Q, R, X, Y, and Z are each preferably a substituted or unsubstituted alkylamino group having 1 to 30 carbon atoms, a substituted or unsubstituted arylamino group having 6 to 30 carbon atoms. As the examples of the substituent, mention may be made of the same ones as the substituents as mentioned when the G is a group capable of further having a substituent. Examples of the amino group may include, for example, amino, methylamino, dimethylamino, anilino, N-methyl-anilino, diphenyl amino, hydroxyethylamino, carboxyethylamino, sulfoethylamino, and 3,5-dicarboxy anilino.

The acylamino groups represented by Q, R, X, Y, and Z are each preferably a formyl amino group, a substituted or unsubstituted alkyl carbonyl amino group having 1 to 30 carbon atoms, or a substituted or unsubstituted aryl carbonyl amino group having 6 to 30 carbon atoms. As the examples of the substituent, mention may be made of the same ones as the substituents as mentioned when the G is a group capable of further having a substituent. Examples of the acylamino group may include, for example, formylamino, acetylamino, pivaloylamino, lauroylamino, bonzoylamino, and 3,4,5-tri-n-octyloxyphenyl carbonyl amino.

The amino carbonyl amino groups represented by Q, R, X, Y, and Z are each preferably a substituted or unsubstituted amino carbonyl amino group having 1 to 30 carbon atoms. As the examples of the substituent, mention may be made of the same ones as the substituents as mentioned when the G is a group capable of further having a substituent. Examples of the amino carbonyl amino group may include, for example, carbamoylamino, N,N-dimethylamino carbonyl amino, N,N-diethylamino carbonyl amino, and morpholino carbonyl amino.

The alkoxy carbonyl amino groups represented by Q, R, X, Y, and Z are each preferably a substituted or unsubstituted alkoxy carbonyl amino group having 2 to 30 carbon atoms. As the examples of the substituent, mention may be made of the same ones as the substituents as mentioned when the G is a group capable of further having a substituent. Examples of the alkoxy carbonyl amino group may include, for example, methoxy carbonyl amino, ethoxy carbonyl amino, t-butoxy carbonyl amino, N-octadecyloxy carbonyl amino, and N-methyl-methoxy carbonyl amino.

The aryloxy carbonyl amino groups represented by Q, R, X, Y, and Z are each preferably a substituted or unsubstituted aryloxy carbonyl amino group having 7 to 30 carbon atoms. As the examples of the substituent, mention may be made of the same ones as the substituents as mentioned when the G is a group capable of further having a substituent. Examples of the aryloxy carbonyl amino group may include, for example, phenoxy carbonyl amino, p-chlorophenoxy carbonyl amino, and m-n-octyloxy phenoxy carbonyl amino.

The sulfamoyl amino groups represented by Q, R, X, Y, and Z are each preferably a substituted or unsubstituted sulfamoyl amino group having 0 to 30 carbon atoms. As the examples of the substituent, mention may be made of the same ones as the substituents as mentioned when the G is a group capable of further having a substituent. Examples of the sulfamoyl amino groups may include, for example, sulfamoyl amino, N,N-dimethylamino sulfonyl amino, N-n-octylamino sulfonylamino.

The alkyl and aryl sulfonyl amino groups represented by Q, R, X, Y, and Z are each preferably a substituted or unsubstituted alkyl sulfonyl amino group having 1 to 30 carbon atoms, a substituted or unsubstituted aryl sulfonyl amino group having 6 to 30 carbon atoms amino group. As the examples of the substituent, mention may be made of the same ones as the substituents as mentioned when the G is a group capable of further having a substituent. Examples of the alkyl sulfonyl amino group and aryl sulfonyl amino group may include, for example, methyl sulfonyl amino, butyl sulfonyl amino, phenyl sulfonyl amino, 2,3,5-trichlorophenyl sulfonyl amino, and p-methyl phenyl sulfonyl amino.

The alkyl thio groups represented by Q, R, X, Y, and Z are each preferably a substituted or unsubstituted alkyl thio group having 1 to 30 carbon atoms. As the examples of the substituent, mention may be made of the same ones as the substituents as mentioned when the G is a group capable of further having a substituent. Examples of the alkyl thio group may include, for example, methyl thio, ethyl thio, and n-hexadecyl thio.

The aryl thio groups represented by Q, R, X, Y, and Z are each preferably a substituted or unsubstituted aryl thio group having 6 to 30 carbon atoms. As the examples of the substituent, mention may be made of the same ones as the substituents as mentioned when the G is a group capable of further having a substituent. Examples of the aryl thio groups may include, for example, phenyl thio, p-chlorophenyl thio, and m-methoxyphenyl thio.

The heterocyclic thio groups represented by Q, R, X, Y, and Z are each preferably a substituted or unsubstituted heterocyclic thio group having 2 to 30. As the examples of the substituent, mention may be made of the same ones as the substituents as mentioned when the G is a group capable of further having a substituent. Examples of the heterocyclic thio groups may include, for example, 2-benzothiazolyl thio, and 1-phenyltetrazol-5 -ylthio.

The sulfamoyl groups represented by Q, R, X, Y, and Z are each preferably a substituted or unsubstituted sulfamoyl group having 0 to 30 carbon atoms. As the examples of the substituent, mention may be made of the same ones as the substituents as mentioned when the G is a group capable of further having a substituent. Examples of the sulfamoyl groups may include, for example, N-ethyl sulfamoyl, N-(3-dodecyloxy propyl)sulfamoyl, N,N-dimethyl sulfamoyl, N-acetyl sulfamoyl, N-benzoyl sulfamoyl, and N-(N'-phenyl carbamoyl)sulfamoyl).

The alkyl and aryl sulfinyl groups represented by Q, R, X, Y, and Z are each preferably a substituted or unsubstituted alkyl sulfinyl group having 1 to 30 carbon atoms, or a substituted or unsubstituted aryl sulfinyl group having 6 to 30 carbon atoms. As the examples of the substituent, mention may be made of the same ones as the substituents as mentioned when the G is a group capable of further having a substituent. Examples of the alkyl and aryl sulfinyl groups may include, for example, methyl sulfinyl, ethyl sulfinyl, phenyl sulfinyl, and p-methyl phenyl sulfinyl.

The alkyl and aryl sulfonyl groups represented by Q, R, X, Y, and Z are each preferably a substituted or unsubstituted alkyl sulfonyl group having 1 to 30 carbon atoms, or a substituted or unsubstituted aryl sulfonyl group having 6 to 30 carbon atoms. As the examples of the substituent, mention may be made of the same ones as the substituents as mentioned when the G is a group capable of further having a substituent. Examples of the alkyl and aryl sulfonyl groups may include, for example, methyl sulfonyl, ethyl sulfonyl, phenyl sulfonyl, and p-toluene sulfonyl.

The acyl groups represented by Q, R, X, Y, and Z are each preferably a formyl group, a substituted or unsubstituted alkyl carbonyl group having 2 to 30, a substituted or unsubstituted aryl carbonyl group having 7 to 30 carbon atoms, a substituted or unsubstituted heterocyclic carbonyl group having 4 to 30 carbon atoms, bonded to a carbonyl group through a carbon atom. As the examples of the substituent, mention may be made of the same ones as the substituents as mentioned when the G is a group capable of further having a substituent. Examples of the acyl groups may include, for example, acetyl, pivaloyl, 2-chloroacetyl, stearoyl, benzoyl, p-n-octyloxy phenyl carbonyl, 2-pyridyl carbonyl, and 2-furyl carbonyl.

The aryloxy carbonyl groups represented by Q, R, X, Y, and Z are each preferably a substituted or unsubstituted aryloxy carbonyl group having 7 to 30 carbon atoms. As the examples of the substituent, mention may be made of the same ones as the substituents as mentioned when the G is a group capable of further having a substituent. Examples of the aryloxy carbonyl group may include, for example, phenoxy carbonyl, o-chlorophenoxy carbonyl, m-nitrophenoxy carbonyl, and p-t-butyl phenoxy carbonyl.

The alkoxy carbonyl groups represented by Q, R, X, Y, and Z are each preferably a substituted or unsubstituted alkoxy carbonyl group having 2 to 30 carbon atoms. As the examples of the substituent, mention may be made of the same ones as the substituents as mentioned when the G is a group capable of further having a substituent. Examples of the alkoxy carbonyl group may include, for example, methoxy carbonyl, ethoxy carbonyl, t-butoxy carbonyl, and n-octadecyloxy carbonyl.

The carbamoyl groups represented by Q, R, X, Y, and Z are each preferably a substituted or unsubstituted carbamoyl group having 1 to 30 carbon atoms. As the examples of the substituent, mention may be made of the same ones as the substituents as mentioned when the G is a group capable of further having a substituent. Examples of the carbamoyl group may include, for example, carbamoyl, N-methyl carbamoyl, N,N-dimethyl carbamoyl, N,N-di-n-octyl carbamoyl, and N-(methyl sulfonyl)carbamoyl.

The phosphino groups represented by Q, R, X, Y, and Z are each preferably a substituted or unsubstituted phosphino group having 2 to 30 carbon atoms. As the examples of the substituent, mention may be made of the same ones as the substituents as mentioned when the G is a group capable of further having a substituent. Examples of the phosphino groups may include, for example, dimethyl phosphino, diphenyl phosphino, and methyl phenoxy phosphino.

The phosphinyl groups represented by Q, R, X, Y, and Z are each preferably a substituted or unsubstituted phosphinyl group having 2 to 30 carbon atoms. As the examples of the substituent, mention may be made of the same ones as the substituents as mentioned when the G is a group capable of further having a substituent. Examples of the phosphinyl groups may include, for example, phosphinyl, dioctyloxy phosphinyl, and diethoxy phosphinyl.

The phosphinyloxy groups represented by Q, R, X, Y, and Z are each preferably a substituted or unsubstituted phosphinyloxy group having 2 to 30 carbon atoms. As the examples of the substituent, mention may be made of the same ones as the substituents as mentioned when the G is a group capable of further having a substituent. Examples of the phosphinyloxy groups may include, for example, diphenoxy phosphinyloxy, and dioctyloxy phosphinyloxy.

The phosphinyl amino groups represented by Q, R, X, Y, and Z are each preferably a substituted or unsubstituted phosphinyl amino group having 2 to 30 carbon atoms. As the examples of the substituent, mention may be made of the same ones as the substituents as mentioned when the G is a group capable of further having a substituent. Examples of the phosphinyl amino group may include, for example, dimethoxy phosphinyl amino, and dimethylamino phosphinyl amino.

The silyl groups represented by Q, R, X, Y, and Z are each preferably a substituted or unsubstituted silyl group having 3 to 30 carbon atoms. As the examples of the substituent, mention may be made of the same ones as the substituents as mentioned when the G is a group capable of further having a substituent. Examples of the silyl groups may include, for example, trimethyl silyl, t-butyldimethyl silyl, and phenyldimethyl silyl.

Examples of the azo groups represented by Q, R, X, Y, and Z may include phenyl azo, 4-methoxyphenyl azo, 4-pivaloylamino phenyl azo, and 2-hydroxy-4-propanoyl phenyl azo.

Examples of the imido group represented by Q, R, X, Y, and Z may include N-succinimido and N-phthalimido.

When Q, R, X, Y, and Z each represent a divalent group, the divalent group is preferably an alkylene group (e.g., methylene, ethylene, propylene, butylene, pentylene), an alkenylene group (e.g., ethenylene or propenylene), an alkynylene group (e.g., ethynylene or propynylene), an arylene group (e.g., phenylene or naphthalene), a divalent heterocyclic group (e.g., a 6-chloro-1,3,5-triazin-2,4-diyl group, a pyrimidine 2,4-diyl group, a quinoxaline-2,3-diyl group, or pyridazine-3,6-diyl), —O—, —CO—, —NR'— (where R' is a hydrogen atom, an alkyl group, or an aryl group), —S—, —SO$_2$—, —SO—, or a combination thereof (e.g., —NHCH$_2$CH$_2$NH—, or —NHCONH—).

An alkylene group, an alkenylene group, an alkynylene group, an arylene group, a divalent heterocyclic group, or an alkyl group or an aryl group of R may have a substituent.

Examples of the substituent are the same as the substituents described for the G.

The alkyl group and the aryl group of the R' are the same as the examples of the substituent of the G.

Further preferably, they are each further preferably an alkylene group having 10 or less carbon atoms, an alkenylene group having 10 or less carbon atoms, an alkynylene group having 10 or less carbon atoms, an arylene group having 6 or more and 10 or less carbon atoms, a divalent heterocyclic group, —S—, —SO—, —SO$_2$—, or a combination thereof (e.g., —SCH$_2$CH$_2$S— or —SCH$_2$CH$_2$CH$_2$S—).

The total number of carbon atoms of the divalent linking group is preferably 0 to 50, more preferably 0 to 30, and most preferably 0 to 10.

When Q, R, X, Y, and Z each represent a trivalent group, the trivalent group is preferably an alkylene group, an alkenylene group, an alkynylene group, an arylene group, a trivalent heterocyclic group, >N—, or a combination thereof (e.g., >NCH$_2$CH$_2$NH— or >NCONH—).

The total number of carbon atoms of the trivalent linking group is preferably 0 to 50, more preferably 0 to 30, and most preferably 0 to 10.

In the formula (I), preferred examples of n is 1 or 2, and in particular preferably 2.

In the formula (I), preferred examples of a substituent of X is an electron attracting group. It is particularly an electron attracting group with a Hammett's substituent constant σp value of 0.20 or more, and more preferably, it is preferably an electron attracting group with a σp value of 0.30 or more. It is an electron attracting group of 1.0 or less as the upper limit.

Specific examples of X which is an electron attracting group with a σp value of 0.20 or more may include an acyl group, an acyloxy group, a carbamoyl group, an alkyloxy carbonyl group, an aryloxy carbonyl group, a cyano group, a nitro group, a dialkyl phosphono group, a diaryl phosphono group, a diaryl phosphinyl group, an alkyl sulfinyl group, an aryl sulfinyl group, an alkyl sulfonyl group, an aryl sulfonyl group, a sulfonyloxy group, an acyl thio group, a sulfamoyl group, a thiocyanate group, a thiocarbonyl group, an alkyl halide group, an alkoxy halide group, an aryloxy halide group, an alkylamino halide group, an alkyl thio halide group, an aryl group substituted with another electron attracting group with a σp value of 0.20 or more, a heterocyclic group, a halogen atom, an azo group, or a selenocyanate group.

As preferred ones of X, mention may be made of an acyl group having 2 to 12 carbon atoms, an acyloxy group having 2 to 12 carbon atoms, a carbamoyl group having 1 to 12 carbon atoms, an alkyloxy carbonyl group having 2 to 12 carbon atoms, an aryloxy carbonyl group having 7 to 18 carbon atoms, a cyano group, a nitro group, an alkyl sulfinyl group having 1 to 12 carbon atoms, an aryl sulfinyl group having 6 to 18 carbon atoms, an alkyl sulfonyl group having 1 to 12 carbon atoms, an aryl sulfonyl group having 6 to 18 carbon atoms, a sulfamoyl group having 0 to 12 carbon atoms, an alkyl halide group having 1 to 12 carbon atoms, an alkyloxy halide group having 1 to 12 carbon atoms, an alkyl thio halide group having 1 to 12 carbon atoms, an aryloxy halide group having 7 to 18 carbon atoms, an aryl group having 7 to 18 carbon atoms, substituted with two or more electron attracting groups with a σp of 0.20 or more, and a heterocyclic group which has 1 to 18 carbon atoms, is 5- to 8-membered, and has a nitrogen atom, an oxygen atom, or a sulfur atom.

Further preferably, mention may be made of a cyano group, an alkyl sulfonyl group having 1 to 12 carbon atoms, an aryl sulfonyl group having 6 to 18 carbon atoms, or a sulfamoyl group having 0 to 12 carbon atoms.

As X, the particularly preferred ones are each a cyano group, an alkyl sulfonyl group having 1 to 12 carbon atoms, or a sulfamoyl group having 0 to 12 carbon atoms. Most preferred is a cyano group, or an alkyl sulfonyl group having 1 to 12 carbon atoms.

In the formula (I), preferred examples of the substituent of Z show a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted aralkyl group, a substituted or unsubstituted aryl group, or a substituted or unsubstituted heterocyclic group.

The detailed examples of the substituent represented by Z are the same as the corresponding substituent examples described for the examples of the heterocyclic group represented by the G, and preferred examples thereof are also the same.

The particularly preferred substituent represented by Z is preferably a substituted aryl group, or a substituted heterocyclic group. Out of these, particularly, a substituted aryl group is preferred.

In the formula (I), preferred examples of the substituent of Q are preferably a hydrogen atom, a substituted or unsubstituted alkyl group, a substituted or unsubstituted acyl group, a substituted or unsubstituted alkyl sulfonyl group, or a substituted or unsubstituted aryl sulfonyl group. Particularly preferred is a hydrogen atom, a substituted or unsubstituted alkyl group, or a substituted or unsubstituted acyl group. Out of these, particularly, a hydrogen atom is preferred.

In the formula (I), R is preferably a substituted or unsubstituted total carbon number C1 to C12 alkyl group, a substituted or unsubstituted total carbon number C6 to C18 aryl group, or a substituted or unsubstituted total carbon number C4 to C12 heterocyclic group. Out of these, a total carbon atom number C1 to C8 straight-chain alkyl group, or branched alkyl group is preferred. Particularly, a secondary or tertiary alkyl group is preferred, and a t-butyl group is most preferred.

In the formula (I), Y is preferably a hydrogen atom, a substituted or unsubstituted total carbon number C1 to C12 alkyl group, a substituted or unsubstituted total carbon number C6 to C18 aryl group, or a substituted or unsubstituted total carbon number C4 to C12 heterocyclic group. Out of these, a hydrogen atom, a total carbon atom number C1 to C8 straight-chain alkyl group, and or branched alkyl group is preferred. Particularly, a hydrogen atom, or a C1 to C8 alkyl group is preferred, and a hydrogen atom is most preferred.

As for the combination of the preferred substituents of the coloring matter represented by the formula (I) of the invention, preferred is a compound in which at least one of various substituents is the preferred group. More preferred is a compound in which a larger number of various substituents are the preferred groups. Most preferred is a compound in which all the substituents are the preferred substituents.

The particularly preferred combinations for the coloring matter represented by the formula (I) of the invention include the following (i) to (vii):

(i) G is preferably a 5- to 8-membered nitrogen-containing heterocyclic ring. Particularly, a S-triazine ring, a pyrimidine ring, a pyridazine ring, a pyrazine ring, a pyridine ring, an imidazole ring, a pyrazole ring, or a pyrrole ring is preferred. Out of these, a S-triazine ring, a pyrimidine ring, a pyridazine ring, or a pyrazine ring is preferred. A S-triazine ring is most preferred.

(ii) R is preferably a substituted or unsubstituted total carbon number C1 to C12 alkyl group, a substituted or unsubstituted total carbon number C6 to C18 aryl group, or a substituted or unsubstituted total carbon number C4 to C12 heterocyclic group. Out of these, preferred is a total carbon atom number C1 to C8 straight-chain alkyl group or branched alkyl group. Particularly, a secondary or tertiary alkyl group is preferred, and a t-butyl group is most preferred.

(iii) X is in particular preferably a cyano group, an alkyl sulfonyl group having 1 to 12 carbon atoms, an aryl sulfonyl group having 6 to 18 carbon atoms, or a sulfamoyl group having 0 to 12 carbon atoms. Out of these, a cyano group, or an alkyl sulfonyl group having 1 to 12 carbon atoms is preferred. Most preferred is a cyano group.

(iv) Y is preferably a hydrogen atom, a substituted or unsubstituted total carbon number C1 to C12 alkyl group, a substituted or unsubstituted total carbon number C6 to C18 aryl group, or a substituted or unsubstituted total carbon number C4 to C12 heterocyclic group. Out of these, a hydrogen atom, a total carbon atom number C1 to C8 straight-chain alkyl group or branched alkyl group is preferred. Particularly, a hydrogen atom or a C1 to C8 alkyl group is preferred. A hydrogen atom is most preferred.

(v) Z is preferably a hydrogen atom, a substituted or unsubstituted alkyl group, a substituted or unsubstituted cycloalkyl group, a substituted or unsubstituted alkenyl group, a substituted or unsubstituted alkynyl group, a substituted or unsubstituted aralkyl group, a substituted or unsubstituted aryl group, or a substituted or unsubstituted heterocyclic group. The particularly preferred substituent is a substituted aryl group or a substituted heterocyclic group. Out of these, particularly, a substituted aryl group is preferred.

(vi) Q is preferably a hydrogen atom, a substituted or unsubstituted alkyl group, a substituted or unsubstituted acyl group, a substituted or unsubstituted alkyl sulfonyl group, or a substituted or unsubstituted aryl sulfonyl group. Particularly, a hydrogen atom, a substituted or unsubstituted alkyl group, or a substituted or unsubstituted acyl group is preferred. Out of these, particularly, a hydrogen atom is preferred.

(vii) n represents an integer of 1 to 3, preferably 1 or 2, and particularly most preferably 2.

Out of the azo coloring matters represented by the formula (I), preferred are the coloring matters represented by the following formulae (1) to (5):

Below, the formula (1) will be described in details.

Formula (1)

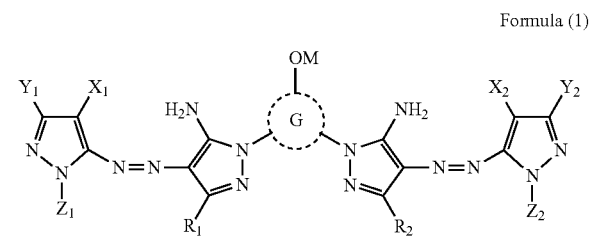

$R_1, R_2, X_1, X_2, Y_1, Y_2, Z_1,$ and $Z_2$ each represent a monovalent group.

The monovalent group represents a hydrogen atom, or a monovalent substituent. Examples of the monovalent substituent are the same as the examples of the monovalent substituent of R,X,Y, and Z in the formula (I), and the preferred examples there of are also the same.

Below, the $R_1, R_2, X_1, X_2, Y_1, Y_2, Z_1,$ and $Z_2$ will be further described in details.

Examples of the substituents of $R_1$ and $R_2$ are each independently the same as the examples of R in the formula (I), and the preferred examples thereof are also the same.

Examples of the substituents of $Y_1$ and $Y_2$ are each independently the same as the examples of Y in the formula (I), and the preferred examples thereof are also the same.

Examples of the substituents of $Z_1$ and $Z_2$ are each independently the same as the examples of Z in the formula (I), and the preferred examples thereof are also the same.

Below, the G will be further described in details.

G represents an atomic group forming a 5- to 8-membered nitrogen-containing heterocyclic ring.

Preferred examples of the 5- to 8-membered nitrogen-containing heterocyclic ring represented by G may include a S-triazine ring, a pyramidine ring, a pyridazine ring, a pyrazine ring, a pyridine ring, an imidazole ring, a pyrazole ring, or a pyrrole ring. Out of these, a S-triazine ring, a pyramidine ring, a pyridazine ring, or a pyrazine ring is more preferred. A S-triazine ring is most preferred.

Below, the M will be further described in details.

M represents a hydrogen atom or a cation.

The cation represented by M is an alkali metal ion, ammonium, or a quaternary ammonium cation, and preferably Li, Na, K, or $NR_4$. However, Rs are an alkyl group and an aryl group, and the same as the examples of the alkyl group and the aryl group represented by R and Y. Out of these, preferred examples of M include Li, Na, K, or $NH_4$, and Li, Na, or K is in particular preferred.

As for the combination of the preferred substituents of the coloring matter represented by the formula (1) of the invention, preferred is a compound in which at least one of various substituents is the preferred group. More preferred is a compound in which a larger number of various substituents are the preferred groups. Most preferred is a compound in which all the substituents are the preferred substituents.

The particularly preferred combinations for the coloring matter represented by the formula (1) of the invention include the following (i) to (vi):

(i) $R_1$ and $R_2$ may be the same or different. A substituted or unsubstituted total carbon number C1 to C12 alkyl group, a substituted or unsubstituted total carbon number C6 to C18 aryl group, or a substituted or unsubstituted total carbon number C4 to C12 heterocyclic group is preferred. Out of these, a total carbon atom number C1 to C8 straight-chain alkyl group or branched alkyl group is preferred. Particularly, a secondary or tertiary alkyl group is preferred, and a t-butyl group is most preferred.

(ii) $X_1$ and $X_2$ may be the same or different. An electron attracting group with a Hammett's substituent constant σp value of 0.20 or more is preferred. Further, an electron attracting group with a σp value of 0.30 or more is preferred. An electron attracting group of 1.0 or less is preferred as the upper limit. Out of these, preferred is a cyano group, an alkyl sulfonyl group having 1 to 12 carbon atoms, an aryl sulfonyl group having 6 to 18 carbon atoms, or a sulfamoyl group having 0 to 12 carbon atoms. Most preferred is a cyano group or an alkyl sulfonyl group having 1 to 12 carbon atoms.

(iii) $Y_1$ and $Y_2$ may be the same or different. A hydrogen atom, a substituted or unsubstituted total carbon number C1 to C12 alkyl group, a substituted or unsubstituted total carbon number C6 to C18 aryl group, or a substituted or unsubstituted total carbon number C4 to C12 heterocyclic group is preferred. Further, a hydrogen atom, or a substituted or unsubstituted alkyl group is preferred. Out of these, a hydrogen atom is most preferred.

(iv) $Z_1$ and $Z_2$ may be the same or different. A substituted or unsubstituted total carbon number C1 to 12C alkyl group, a substituted or unsubstituted total carbon number C6 to C18 aryl group, or a substituted or unsubstituted total carbon number C4 to C12 heterocyclic group is preferred. Further, a substituted or unsubstituted aryl group, or a substituted or unsubstituted heterocyclic group is preferred. Particularly, a substituted aryl group is most preferred.

(v) G represents an atomic group forming a 5- to 8-membered nitrogen-containing heterocyclic ring. Preferred examples of the 5- to 8-membered nitrogen-containing heterocyclic ring include a S-triazine ring, a pyramidine ring, a pyridazine ring, a pyrazine ring, a pyridine ring, an imidazole ring, a pyrazole ring, or a pyrrole ring. Out of these, a S-triazine ring, a pyramidine ring, a pyridazine ring, or a pyrazine ring is more preferred. A S-triazine ring is most preferred.

(vi) M is preferably a hydrogen atom or a cation, in particular preferably a hydrogen atom, an alkali metal ion, ammonium, or a quaternary ammonium cation, and further preferably Li, Na, K, or $NH_4$.

Below, the formula (2) will be described in details.

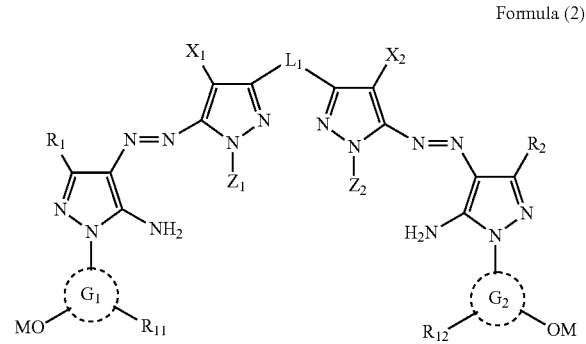

Formula (2)

$R_1$, $R_2$, $R_{11}$, $R_{12}$, $X_1$, $X_2$, $Z_1$, and $Z_2$ each represent a monovalent group.

The monovalent group represents a hydrogen atom or a monovalent substituent.

$L_1$ represents a divalent linking group.

$G_1$ and $G_2$ each independently represent an atomic group forming a 5- to 8-membered nitrogen-containing heterocyclic ring.

M represents a hydrogen atom or a cation.

Below, the formula (2) will be further described in details.

In the formula (2), preferred examples of the substituents of $R_1$ and $R_2$ are the same as the examples of the substituents of $R_1$, $R_2$, $Y_1$, and $Y_2$ described for the formula (1), and the preferred examples thereof are also the same.

In the formula (2), preferred examples of the substituents of $X_1$ and $X_2$ are the same as the examples of the substituents of $X_1$ and $X_2$ described for the formula (1), and the preferred examples thereof are also the same.

In the formula (2), preferred examples of the substituents of $Z_1$ and $Z_2$ are the same as the examples of the substituents of $Z_1$ and $Z_2$ described for the formula (1), and the preferred examples thereof are also the same.

In the formula (2), preferred examples of the substituents of $G_1$ and $G_2$ are the same as the examples of the substituents of G described for the formula (1), and the preferred examples thereof are also the same.

In the formula (2), preferred examples of M are the same as the examples of M described for the formula (1), and the preferred examples thereof are also the same.

In the formula (2), preferred examples of the substituents of $R_{11}$ and $R_{12}$ are the same as the examples of the substituents of $R_1$, $R_2$, $Y_1$, and $Y_2$ described for the formula (1). Preferred examples thereof may include a —OM group (where M is a hydrogen atom or a cation), a substituted or unsubstituted amino group; an alkylamino group having 1 to 12 carbon atoms, an arylamino group having 6 to 18 carbon atoms, a substituted or unsubstituted alkyl thio group having 1 to 12 carbon atoms, and a substituted or unsubstituted aryl thio group having 6 to 18 carbon atoms.

In the formula (2), the divalent linking group represented by $L_1$ is preferably an alkylene group (e.g., methylene, ethylene, propylene, butylene, or pentylene), an alkenylene group (e.g., ethenylene or propenylene), an alkynylene group (e.g., ethynylene or propynylene), an arylene group (e.g., phenylene or naphthylene), a divalent heterocyclic group (e.g., a 6-chloro-1,3,5-triazine-2,4-diyl group, a pyrimidine 2,4-diyl group, a quinoxaline-2,3-diyl group, or a pyridazine-3,6-diyl), —O—, —CO—, —NR— (where R is a hydrogen atom, an alkyl group, or an aryl group), —S—, —SO$_2$—, —SO—, or a combination thereof (e.g., —NHCH$_2$CH$_2$NH— or —NHCONH—).

An alkylene group, an alkenylene group, an alkynylene group, an arylene group, a divalent heterocyclic group, an alkyl group or an aryl group of R may each have a substituent.

Examples of the substituent are the same as the substituents of $R_1$, $R_2$, $Y_1$, and $Y_2$ in the formula (1).

The alkyl groups and the aryl groups of the R are the same as the examples of the substituents of $R_1$, $R_2$, $Y_1$, and $Y_2$ in the formula (1).

Further preferably, they are each further preferably an alkylene group having 10 or less carbon atoms, an alkenylene group having 10 or less carbon atoms, an alkynylene group having 10 or less carbon atoms, an arylene group having 6 or more and 10 or less carbon atoms, —S—, —SO—, —SO$_2$—, or a combination thereof (e.g., —SCH$_2$CH$_2$S—, or —SCH$_2$CH$_2$CH$_2$S).

The total number of carbon atoms of the divalent linking group is preferably 0 to 50, more preferably 0 to 30, and most preferably 0 to 10.

As for the combination of the preferred substituents of the coloring matter represented by the formula (2) of the invention, preferred is a compound in which at least one of various substituents is the preferred group. More preferred is a compound in which a larger number of various substituents are the preferred groups. Most preferred is a compound in which all the substituents are the preferred substituents.

The particularly preferred combinations for the coloring matter represented by the formula (2) of the invention include the following (i) to (vii):

(i) $R_1$ and $R_2$ may be the same or different. A substituted or unsubstituted total carbon number C1 to C12 alkyl group, a substituted or unsubstituted total carbon number C6 to C18 aryl group, or a substituted or unsubstituted total carbon number C4 to C12 heterocyclic group is preferred. Out of these, a total carbon atom number C1 to C8 straight-chain alkyl group or branched alkyl group is preferred. Particularly, a secondary or tertiary alkyl group is preferred, and a t-butyl group is most preferred.

(ii) $X_1$ and $X_2$ may be the same or different. An electron attracting group with a Hammett's substituent constant σp value of 0.20 or more is preferred. Further, an electron attracting group of 0.30 or more is preferred. An electron attracting group of 1.0 or less is preferred as the upper limit. Out of these, preferred is a cyano group, an alkyl sulfonyl group having 1 to 12 carbon atoms, an aryl sulfonyl group having 6 to 18 carbon atoms, or a sulfamoyl group having 0 to 12 carbon atoms. Most preferred is a cyano group or an alkyl sulfonyl group having 1 to 12 carbon atoms.

(iii) $Z_1$ and $Z_2$ may be the same or different. A substituted or unsubstituted total carbon number C1 to C12 alkyl group, a substituted or unsubstituted total carbon number C6 to C18 aryl group, or a substituted or unsubstituted total carbon number C4 to C12 heterocyclic group is preferred. Further, a substituted or unsubstituted aryl group, or a substituted or unsubstituted heterocyclic group is preferred. Particularly, a substituted aryl group is most preferred.

(iv) $G_1$ and $G_2$ may be the same or different, and each represent an atomic group forming a 5- to 8-membered nitrogen-containing heterocyclic ring. Preferred examples of the 5- to 8-membered nitrogen-containing heterocyclic ring include a S-triazine ring, a pyramidine ring, a pyridazine ring, a pyrazine ring, a pyridine ring, an imidazole ring, a pyrazole ring, or a pyrrole ring. Out of these, a S-triazine ring, a pyramidine ring, a pyridazine ring, or a pyrazine ring is more preferred. A S-triazine ring is most preferred.

(v) M is preferably a hydrogen atom or a cation, in particular preferably a hydrogen atom, an alkali metal ion, ammonium, or a quaternary ammonium cation, and further preferably Li, Na, K, or NH$_4$.

(vi) $R_{11}$ and $R_{12}$ may be the same or different. They are each preferably a —OM group (where M is a hydrogen atom or a cation), a substituted or unsubstituted amino group (an alkylamino group having 1 to 12 carbon atoms, an arylamino group having 6 to 18 carbon atoms), a substituted or unsubstituted alkyl thio group having 1 to 12 carbon atoms, or a substituted or unsubstituted aryl thio group having 6 to 18 carbon atoms. Out of these, an unsubstituted amino group, an alkylamino group having 1 to 12 carbon atoms, an arylamino group having 6 to 18 carbon atoms, a substituted or unsubstituted alkyl thio group having 1 to 12 carbon atoms, or a substituted or unsubstituted aryl thio group having 6 to 18 carbon atoms is preferred. Particularly, an unsubstituted amino group, a dialkylamino group having 1 to 12 carbon atoms, an arylamino group having 6 to 18 carbon atoms, or a substituted or unsubstituted alkyl thio group having 1 to 12 carbon atoms is preferred.

(vii) $L_1$ is preferably an alkylene group having 10 or less carbon atoms, an alkenylene group having 10 or less carbon atoms, an alkynylene group having 10 or less carbon atoms, an arylene group having 6 or more and 10 or less carbon atoms, —S—, —SO—, —SO$_2$—, or a combination thereof (e.g., —SCH$_2$CH$_2$S—, or —SCH$_2$CH$_2$CH$_2$S—). It is further preferably an alkylene group having 10 or less carbon atoms, an arylene group having 6 or more and 10 or less carbon atoms, —S—, —SO—, —SO$_2$—, or a combination thereof (e.g., —SCH$_2$CH$_2$S—, or —SCH$_2$CH$_2$CH$_2$S—). It is in particular preferably an alkylene group having 10 or less carbon atoms, —SCH$_2$CH$_2$S—, or —SCH$_2$CH$_2$CH$_2$S—.

Below, the formula (3) will be described in details.

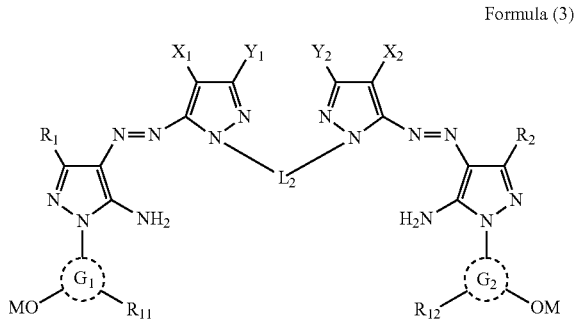

Formula (3)

$R_1$, $R_2$, $R_{11}$, $R_{12}$, $X_1$, $X_2$, $Y_1$, and $Y_2$ each represent a monovalent group.

The monovalent group represents a hydrogen atom or a monovalent substituent.

$L_2$ represents a divalent linking group.

$G_1$ and $G_2$ each independently represent an atomic group forming a 5- to 8-membered nitrogen-containing heterocyclic ring.

M represents a hydrogen atom or a cation.

Below, the formula (3) will be further described in details.

In the formula (3), preferred examples of the substituents of $R_1$, $R_2$, $Y_1$, and $Y_2$ are the same as the examples of the substituents of $R_1$, $R_2$, $Y_1$, and $Y_2$ described for the formula (1), and the preferred examples thereof are also the same.

In the formula (3), preferred examples of the substituents of $X_1$ and $X_2$ are the same as the examples of the substituents of $X_1$ and $X_2$ described for the formula (1), and the preferred examples thereof are also the same.

In the formula (3), preferred examples of the substituents of $G_1$ and $G_2$ are the same as the examples of the substituents of G described for the formula (1), and the preferred examples thereof are also the same.

In the formula (3), preferred examples of the substituents of M are the same as the examples of the substituents of M described for the formula (1), and the preferred examples thereof are also the same.

In the formula (3), preferred examples of the substituents of $R_{11}$ and $R_{12}$ are the same as the examples of the substituents of $R_1$ and $R_2$ described for the formula (2), and the preferred examples thereof are also the same.

In the formula (3), the divalent linking groups represented by $L_2$ are the same as the examples $L_1$ described for the formula (2), and the preferred examples thereof are also the same.

As for the combination of the preferred substituents of the coloring matter represented by the formula (3) of the invention, preferred is a compound in which at least one of various substituents is the preferred group. More preferred is a compound in which a larger number of various substituents are the preferred groups. Most preferred is a compound in which all the substituents are the preferred substituents.

The particularly preferred combinations for the coloring matter represented by the formula (3) of the invention include the following (i) to (vii):

(i) $R_1$ and $R_2$ may be the same or different. A substituted or unsubstituted total carbon number C1 to C12 alkyl group, a substituted or unsubstituted total carbon number C6 to C18 aryl group, or a substituted or unsubstituted total carbon number C4 to C12 heterocyclic group is preferred. Out of these, a total carbon atom number C1 to C8 straight-chain alkyl group or branched alkyl group is preferred. Particularly, a secondary or tertiary alkyl group is preferred, and a t-butyl group is most preferred.

(ii) $X_1$ and $X_2$ may be the same or different. An electron attracting group with a Hammett's substituent constant σp value of 0.20 or more is preferred. Further, an electron attracting group 0.30 or more is preferred. An electron attracting group of 1.0 or less is preferred as the upper limit. Out of these, preferred is a cyano group, an alkyl sulfonyl group having 1 to 12 carbon atoms, an aryl sulfonyl group having 6 to 18 carbon atoms, or a sulfamoyl group having 0 to 12 carbon atoms. Most preferred is a cyano group or an alkyl sulfonyl group having 1 to 12 carbon atoms.

(iii) $Y_1$ and $Y_2$ may be the same or different. A hydrogen atom, a substituted or unsubstituted total carbon number C1 to C12 alkyl group, a substituted or unsubstituted total carbon number C6 to C18 aryl group, or a substituted or unsubstituted total carbon number C4 to C12 heterocyclic group is preferred. Further, a hydrogen atom, or a substituted or unsubstituted alkyl group is preferred. Out of these, a hydrogen atom is most preferred.

(iv) $G_1$ and $G_2$ may be the same or different, and each represent an atomic group forming a 5- to 8-membered nitrogen-containing heterocyclic ring. Preferred examples of the 5- to 8-membered nitrogen-containing heterocyclic ring include a S-triazine ring, a pyramidine ring, a pyridazine ring, a pyrazine ring, a pyridine ring, an imidazole ring, a pyrazole ring, or a pyrrole ring. Out of these, a S-triazine ring, a pyramidine ring, a pyridazine ring, or a pyrazine ring is more preferred. A S-triazine ring is most preferred.

(v) M is preferably a hydrogen atom or a cation, in particular preferably a hydrogen atom, an alkali metal ion, ammonium, or a quaternary ammonium cation, and further preferably Li, Na, K, or $NH_4$.

(vi) $R_{11}$ and $R_{12}$ may be the same or different. They are each preferably a —OM group (where M is a hydrogen atom or a cation), a substituted or unsubstituted amino group (such as an alkylamino group having 1 to 12 carbon atoms, or an arylamino group having 6 to 18 carbon atoms), a substituted or unsubstituted alkyl thio group having 1 to 12 carbon atoms, and a substituted or unsubstituted aryl thio group having 6 to 18 carbon atoms. Out of these, an unsubstituted amino group, an alkylamino group having 1 to 12 carbon atoms, an arylamino group having 6 to 18 carbon atoms, a substituted or unsubstituted alkyl thio group having 1 to 12 carbon atoms, or a substituted or unsubstituted aryl thio group having 6 to 18 carbon atoms is preferred. Particularly, an unsubstituted amino group, a dialkylamino group having 1 to 12 carbon atoms, an arylamino group having 6 to 18 carbon atoms, or a substituted or unsubstituted alkyl thio group having 1 to 12 is preferred.

(vii) $L_2$ is preferably an alkylene group having 10 or less carbon atoms, an alkenylene group having 10 or less carbon atoms, an alkynylene group having 10 or less carbon atoms, an arylene group having 6 or more and 10 or less carbon atoms, —S—, —SO—, —$SO_2$—, or a combination thereof (e.g., —$SCH_2CH_2S$—, or —$SCH_2CH_2CH_2S$—). It is further preferably an alkylene group having 10 or less carbon atoms, an arylene group having 6 or more and 10 or less carbon atoms, —S—, —SO—, —$SO_2$—, or a combination thereof (e.g., —$SCH_2CH_2S$—, or —$SCH_2CH_2CH_2S$—). It is in particular preferably an alkylene group having 10 or less carbon atoms, —$SCH_2CH_2S$—, or —$SCH_2CH_2CH_2S$—.

Below, the formula (4) will be described in details.

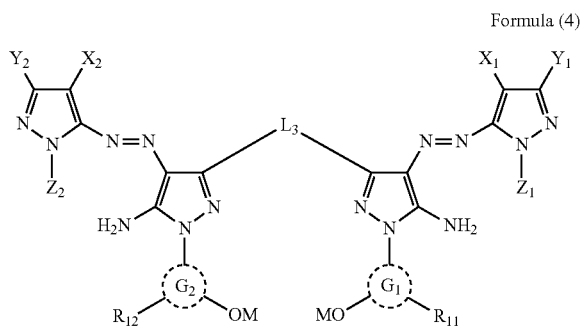

Formula (4)

$R_{11}$, $R_{12}$, $X_1$, $X_2$, $Y_1$, $Y_2$, $Z_1$, and $Z_2$ each represent a monovalent group.

The monovalent group represents a hydrogen atom or a monovalent substituent.

$L_3$ represents a divalent linking group.

$G_1$ and $G_2$ each independently represent an atomic group forming a 5- to 8-membered nitrogen-containing heterocyclic ring.

M represents a hydrogen atom or a cation.

Below, the formula (4) will be further described in details.

In the formula (4), preferred examples of the substituents of $Y_1$, and $Y_2$ are the same as the examples of the substituents of $R_1$, $R_2$, $Y_1$, and $Y_2$ described for the formula (1), and the preferred examples thereof are also the same.

In the formula (4), preferred examples of the substituents of $X_1$ and $X_2$ are the same as the examples of the substituents of $X_1$ and $X_2$ described for the formula (1), and the preferred examples thereof are also the same.

In the formula (4), preferred examples of the substituents of $G_1$ and $G_2$ are the same as the examples of the substituents of G described for the formula (1), and the preferred examples thereof are also the same.

In the formula (4), preferred examples of M are the same as the examples of M described for the formula (1), and the preferred examples thereof are also the same.

In the formula (4), preferred examples of the substituents of $R_{11}$ and $R_{12}$ are the same as the examples of the substituents of $R_{11}$ and $R_{12}$ described for the formula (2), and the preferred examples thereof are also the same.

In the formula (4), the divalent linking groups represented by $L_3$ are the same as the examples of the substituents of $L_1$ described for the formula (2), and the preferred examples thereof are also the same.

As for the combination of the preferred substituents of the coloring matter represented by the formula (4) of the invention, preferred is a compound in which at least one of various substituents is the preferred group. More preferred is a compound in which a larger number of various substituents are the preferred groups. Most preferred is a compound in which all the substituents are the preferred substituents.

The particularly preferred combinations for the coloring matter represented by the formula (4) of the invention include the following (i) to (vii):

(i) $Y_1$ and $Y_2$ may be the same or different. A hydrogen atom, a substituted or unsubstituted total carbon number C1 to C12 alkyl group, a substituted or unsubstituted total carbon number C6 to C18 aryl group, or a substituted or unsubstituted total carbon number C4 to C12 heterocyclic group is preferred. Further, a hydrogen atom, or a substituted or unsubstituted alkyl group is preferred. Out of these, a hydrogen atom is most preferred.

(ii) $X_1$ and $X_2$ may be the same or different. An electron attracting group with a Hammett's substituent constant σp value of 0.20 or more is preferred. Further, an electron attracting group of 0.30 or more is preferred. An electron attracting group of 1.0 or less is preferred as the upper limit. Out of these, preferred is a cyano group, an alkyl sulfonyl group having 1 to 12 carbon atoms, an aryl sulfonyl group having 6 to 18 carbon atoms, or a sulfamoyl group having 0 to 12 carbon atoms. Most preferred is a cyano group or an alkyl sulfonyl group having 1 to 12 carbon atoms.

(iii) $Z_1$ and $Z_2$ may be the same or different. A substituted or unsubstituted total carbon number C1 to 12C alkyl group, a substituted or unsubstituted total carbon number C6 to C18 aryl group, or a substituted or unsubstituted total carbon number C4 to C12 heterocyclic group is preferred. Further, a substituted or unsubstituted aryl group, or a substituted or unsubstituted heterocyclic group is preferred. Particularly, a substituted aryl group is most preferred.

(iv) $G_1$ and $G_2$ may be the same or different, and each represent an atomic group forming a 5- to 8-membered nitrogen-containing heterocyclic ring. Preferred examples of the 5- to 8-membered nitrogen-containing heterocyclic ring include a S-triazine ring, a pyramidine ring, a pyridazine ring, a pyrazine ring, a pyridine ring, an imidazole ring, a pyrazole ring, or a pyrrole ring. Out of these, a S-triazine ring, a pyramidine ring, a pyridazine ring, or a pyrazine ring is more preferred. A S-triazine ring is most preferred.

(v) M is preferably a hydrogen atom or a cation, in particular preferably a hydrogen atom, an alkali metal ion, ammonium, or a quaternary ammonium cation, and further preferably Li, Na, K, or $NH_4$.

(vi) $R_{11}$ and $R_{12}$ may be the same or different. They are each preferably a —OM group (where M is a hydrogen atom or a cation), a substituted or unsubstituted amino group (such as an alkylamino group having 1 to 12 carbon atoms, or an arylamino group having 6 to 18 carbon atoms), a substituted or unsubstituted alkyl thio group having 1 to 12 carbon atoms, and a substituted or unsubstituted aryl thio group having 6 to 18 carbon atoms. Out of these, an unsubstituted amino group, an alkylamino group having 1 to 12 carbon atoms, an arylamino group having 6 to 18 carbon atoms, a substituted or unsubstituted alkyl thio group having 1 to 12 carbon atoms, or a substituted or unsubstituted aryl thio group having 6 to 18 carbon atoms is preferred. Particularly, an unsubstituted amino group, a dialkylamino group having 1 to 12 carbon atoms, an arylamino group having 6 to 18 carbon atoms, or a substituted or unsubstituted alkyl thio group having 1 to 12 is preferred.

(vii) $L_3$ is preferably an alkylene group having 10 or less carbon atoms, an alkenylene group having 10 or less carbon atoms, an alkynylene group having 10 or less carbon atoms, an arylene group having 6 or more and 10 or less carbon atoms, —S—, —SO—, —$SO_2$—, or a combination thereof (e.g., —$SCH_2CH_2S$—, or —$SCH_2CH_2CH_2S$—). It is further preferably an alkylene group having 10 or less carbon atoms, an arylene group having 6 or more and 10 or less carbon atoms, —S—, —SO—, —$SO_2$—, or a combination thereof (e.g., —$SCH_2CH_2S$—, or —$SCH_2CH_2CH_2S$—). It is in particular preferably an alkylene group having 10 or less carbon atoms, —$SCH_2CH_2S$—, or —$SCH_2CH_2CH_2S$—.

Below, the formula (5) will be described in details.

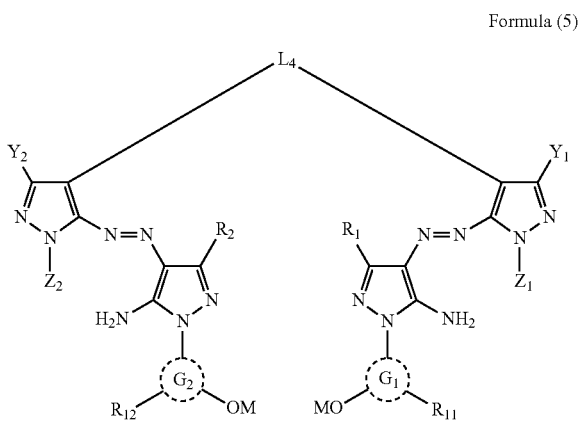

Formula (5)

$R_1$, $R_2$, $R_{11}$, $R_{12}$, $Y_1$, $Y_2$, $Z_1$, and $Z_2$ each represent a monovalent group.

The monovalent group represents a hydrogen atom or a monovalent substituent.

$L_4$ represents a divalent linking group.

$G_1$ and $G_2$ each independently represent an atomic group forming a 5- to 8-membered nitrogen-containing heterocyclic ring.

M represents a hydrogen atom or a cation.

Below, the formula (5) will be further described in details.

In the formula (5), preferred examples of the substituents of $R_1$, $R_2$, $Y_1$, and $Y_2$ are the same as the examples of the substituents of $R_1$, $R_2$, $Y_1$, and $Y_2$ described for the formula (1), and the preferred examples thereof are also the same.

In the formula (5), preferred examples of the substituents of $Z_1$ and $Z_2$ are the same as the examples of the substituents of $Z_1$ and $Z_2$ described for the formula (1), and the preferred examples thereof are also the same.

In the formula (5), preferred examples of $G_1$ and $G_2$ are the same as the examples of the substituents of G described for the formula (1), and the preferred examples thereof are also the same.

In the formula (5), preferred examples of M are the same as the examples of M described for the formula (1), and the preferred examples thereof are also the same.

In the formula (5), preferred examples of the substituents of $R_{11}$ and $R_{12}$ are the same as the examples of the substituents of $R_{11}$ and $R_{12}$ described for the formula (2), and the preferred examples thereof are also the same.

In the formula (5), the divalent linking groups represented by $L_4$ are the same as the examples of the substituents of $L_1$ described for the formula (2), and the preferred examples thereof are also the same.

As for the combination of the preferred substituents of the coloring matter represented by the formula (5) of the invention, preferred is a compound in which at least one of various substituents is the preferred group. More preferred is a compound in which a larger number of various substituents are the preferred groups. Most preferred is a compound in which all the substituents are the preferred substituents.

The particularly preferred combinations for the coloring matter represented by the formula (5) of the invention include the following (i) to (vii):

(i) $R_1$ and $R_2$ may be the same or different. A substituted or unsubstituted total carbon number C1 to C12 alkyl group, a substituted or unsubstituted total carbon number C6 to C18 aryl group, or a substituted or unsubstituted total carbon number C4 to C12 heterocyclic group is preferred. Out of these, a total carbon atom number C1 to C8 straight-chain alkyl group or branched alkyl group is preferred. Particularly, a secondary or tertiary alkyl group is preferred, and a t-butyl group is most preferred.

(ii) $Y_1$ and $Y_2$ may be the same or different. A hydrogen atom, a substituted or unsubstituted total carbon number C1 to C12 alkyl group, a substituted or unsubstituted total carbon number C6 to C18 aryl group, or a substituted or unsubstituted total carbon number C4 to C12 heterocyclic group is preferred. Further, a hydrogen atom, or a substituted or unsubstituted alkyl group is preferred. Out of these, a hydrogen atom is most preferred.

(iii) $Z_1$ and $Z_2$ may be the same or different. A substituted or unsubstituted total carbon number C1 to 12C alkyl group, a substituted or unsubstituted total carbon number C6 to C18 aryl group, or a substituted or unsubstituted total carbon number C4 to C12 heterocyclic group is preferred. Further, a substituted or unsubstituted aryl group, or a substituted or unsubstituted heterocyclic group is preferred. Particularly, a substituted aryl group is most preferred.

(iv) $G_1$ and $G_2$ may be the same or different, and each represent an atomic group forming a 5- to 8-membered nitrogen-containing heterocyclic ring. Preferred examples of the 5- to 8-membered nitrogen-containing heterocyclic ring include a S-triazine ring, a pyramidine ring, a pyridazine ring, a pyrazine ring, a pyridine ring, an imidazole ring, a pyrazole ring, or a pyrrole ring. Out of these, a S-triazine ring, a pyramidine ring, a pyridazine ring, or a pyrazine ring is more preferred. A S-triazine ring is most preferred.

(v) M is preferably a hydrogen atom or a cation, in particular preferably a hydrogen atom, an alkali metal ion, ammonium, or a quaternary ammonium cation, and further preferably Li, Na, K, or $NH_4$.

(vi) $R_{11}$ and $R_{12}$ may be the same or different. They are each preferably a —OM group (where M is a hydrogen atom or a cation), a substituted or unsubstituted amino group; an alkylamino group having 1 to 12 carbon atoms, an arylamino group having 6 to 18 carbon atoms, a substituted or unsubstituted alkyl thio group having 1 to 12 carbon atoms, and a substituted or unsubstituted aryl thio group having 6 to 18 carbon atoms. Out of these, an unsubstituted amino group, an alkylamino group having 1 to 12 carbon atoms, an arylamino group having 6 to 18 carbon atoms, a substituted or unsubstituted alkyl thio group having 1 to 12 carbon atoms, or a substituted or unsubstituted aryl thio group having 6 to 18 carbon atoms is preferred. Particularly, an unsubstituted amino group, a dialkylamino group having 1 to 12 carbon atoms, an arylamino group having 6 to 18 carbon atoms, or a substituted or unsubstituted alkyl thio group having 1 to 12 is preferred.

(vii) $L_4$ is preferably a divalent linking group, and it is preferably an electron attracting group with a Hammett's substituent constant σp value of 0.20 or more, and further preferably an electron attracting group of 0.30 or more. An electron attracting group of 1.0 or less is preferred as the upper limit. Out of these, preferred is an alkyl sulfonyl group having 1 to 12 carbon atoms: $\{-SO_2-(CH_2)_n-O_2S-;$ n=an integer of 1 to 10$\}$, or an aryl sulfonyl group having 6 to 18 carbon atoms: $\{-SO_2-Ar-OS-;$ where Ar is preferably a substituted or unsubstituted aryl group, and most preferably an alkyl sulfonyl group having 1 to 12 carbon atoms: $\{-SO_2-(CH_2)_n-O_2S-;$ n=an integer of 1 to 5$\}$.

Out of the azo coloring matters represented by the formula (I), preferred are the coloring matters represented by the following formula (6):

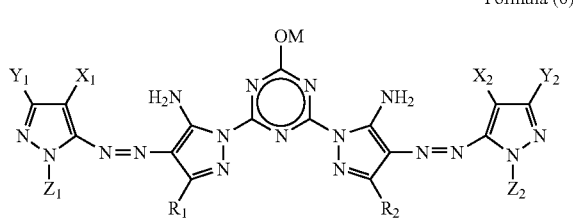

Formula (6)

Below, the formula (6) will be described in details.

$R_1$, $R_2$, $Y_1$, and $Y_2$ each represent a monovalent group, $X_1$ and $X_2$ each independently represent an electron attracting group with a Hammett's substituent constant σp value of 0.20 or more. $Z_1$ and $Z_2$ each independently represent a hydrogen atom, a substituted or unsubstituted alkyl group, a substituted or unsubstituted alkenyl group, a substituted or unsubstituted alkynyl group, a substituted or unsubstituted aralkyl group, a substituted or unsubstituted aryl group, or a substituted or unsubstituted heterocyclic group. M represents a hydrogen atom or a cation.

Below, $R_1$, $R_2$, $X_1$, $X_2$, $Y_1$, $Y_2$, $Z_1$, $Z_2$, and M will be described in details.

Examples of the substituents of $R_1$, $R_2$, $Y_1$, and $Y_2$ are the same as the examples of the substituents of $R_1$, $R_2$, $Y_1$, and $Y_2$ described in the formula (1), and the preferred examples thereof are also the same.

Examples of the substituents of $X_1$ and $X_2$ are the same as the examples of the substituents of $X_1$ and $X_2$ described for the formula (1), and the preferred examples thereof are also the same.

Examples of the substituents of $Z_1$ and $Z_2$ are the same as the examples of the substituents of $Z_1$ and $Z_2$ described in the formula (1), and the preferred examples thereof are also the same.

Examples of M are the same as the examples of M described in the formula (1), and the preferred examples thereof are also the same.

As for the combination of the preferred substituents of the coloring matter represented by the formula (6) of the invention, preferred is a compound in which at least one of various substituents is the preferred group. More preferred is a compound in which a larger number of various substituents are the preferred groups. Most preferred is a compound in which all the substituents are the preferred substituents.

The particularly preferred combinations for the coloring matter represented by the formula (6) of the invention include the following (i) to (vi):

(i) $R_1$ and $R_2$ may be the same or different. A substituted or unsubstituted total carbon number C1 to C12 alkyl group, a substituted or unsubstituted total carbon number C6 to C18 aryl group, or a substituted or unsubstituted total carbon number C4 to C12 heterocyclic group is preferred. Out of these, a total carbon atom number C1 to C8 straight-chain alkyl group or branched alkyl group is preferred. Particularly, a secondary or tertiary alkyl group is preferred, and a t-butyl group is most preferred.

(ii) $X_1$ and $X_2$ may be the same or different. An electron attracting group with a Hammett's substituent constant σp value of 0.20 or more is preferred. Further, an electron attracting group of 0.30 or more is preferred. An electron attracting group of 1.0 or less is preferred as the upper limit. Out of these, preferred is a cyano group, an alkyl sulfonyl group having 1 to 12 carbon atoms, an aryl sulfonyl group having 6 to 18 carbon atoms, or a sulfamoyl group having 0 to 12 carbon atoms. Most preferred is a cyano group or an alkyl sulfonyl group having 1 to 12 carbon atoms.

(iii) $Y_1$ and $Y_2$ may be the same or different. A hydrogen atom, a substituted or unsubstituted total carbon number C1 to C12 alkyl group, a substituted or unsubstituted total carbon number C6 to C18 aryl group, or a substituted or unsubstituted total carbon number C4 to C12 heterocyclic group is preferred. Further, a hydrogen atom, or a substituted or unsubstituted alkyl group is preferred. Out of these, a hydrogen atom is most preferred.

(iv) $Z_1$ and $Z_2$ may be the same or different. A substituted or unsubstituted total carbon number C1 to 12C alkyl group, a substituted or unsubstituted total carbon number C6 to C18 aryl group, or a substituted or unsubstituted total carbon number C4 to C12 heterocyclic group is preferred. Further, a substituted or unsubstituted aryl group, or a substituted or unsubstituted heterocyclic group is preferred. Particularly, a substituted aryl group is most preferred.

(v) M is preferably a hydrogen atom or a cation, in particular preferably a hydrogen atom, an alkali metal ion, ammonium, or a quaternary ammonium cation, and further preferably Li, Na, K, or $NH_4$.

In the invention, when the compounds represented by the formulae (I), (1), (2), (3), (4), (5), and (6) are required to have hydrophilicity, each compound preferably has two or more ionic hydrophilic groups in the molecule, further preferably has 2 to 10 ionic hydrophilic groups, and in particular preferably has 3 to 6 hydrophilic groups.

However, when water is not used as the medium, the compound is not required to have an ionic hydrophilic group.

As the ionic hydrophilic group, any group is acceptable so long as it is an ionic dissociation group. Specifically, mention may be made of a sulfo group, a carboxyl group (including a salt thereof), a hydroxyl group (which may be in the form of a salt), a phosphono group (which may be in the form of a salt), or a quaternary ammonium.

Preferred is a sulfo group, a carboxyl group, or a hydroxyl group (including a salt thereof).

When the ionic hydrophilic group is a salt, preferred countercations are an alkali metal (e.g., lithium, sodium, or potassium), ammonium, and an organic cation (e.g., pyridinium, tetramethyl ammonium, or guadinium). Out of these, an alkali metal is preferred. Particularly, for a sulfo group, a lithium salt is preferred, and for a carboxy group, a sodium salt and or a potassium salt is preferred.

As for the water soluble coloring matter represented by the formulae (I), (1), (2), (3), (4), (5), and (6), from the viewpoint of color reproduction, it preferably has a maximum absorption wavelength (λmax) of 380 to 490 nm in $H_2O$, further preferably has a λmax of 400 to 480 nm, and in particular preferably has a λmax of 420 to 460 nm.

Specific examples of the coloring matter represented by the formulae (I), (1), (2), (3), (4), (5), and (6) (exemplified coloring matters DYE-1 to -26) will be shown below. However, the coloring matters for use in the invention are not limited to the following examples.

Whereas, the structure of the following specific examples is shown in the form of a free acid. However, it is naturally understood that each example may be used in the form of a given salt.

As preferred countercation, mention may be made of an alkali metal (e.g., lithium, sodium, or potassium), ammonium, or an organic cation (e.g., pyridinium, tetramethyl ammonium, or guadinium).
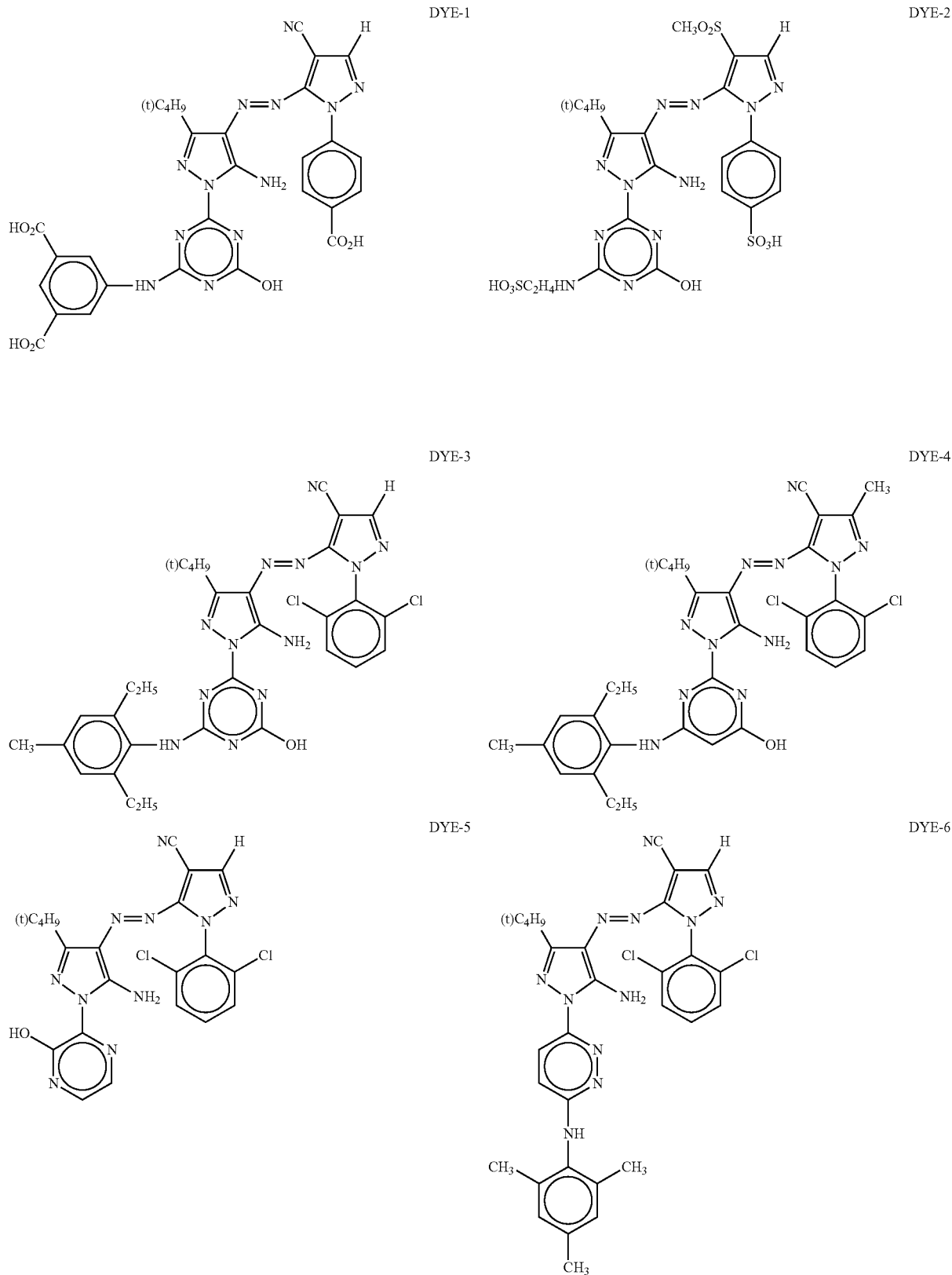

-continued
DYE-7
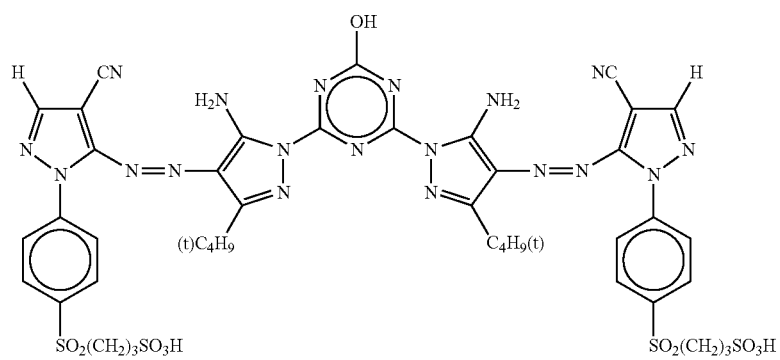
DYE-8
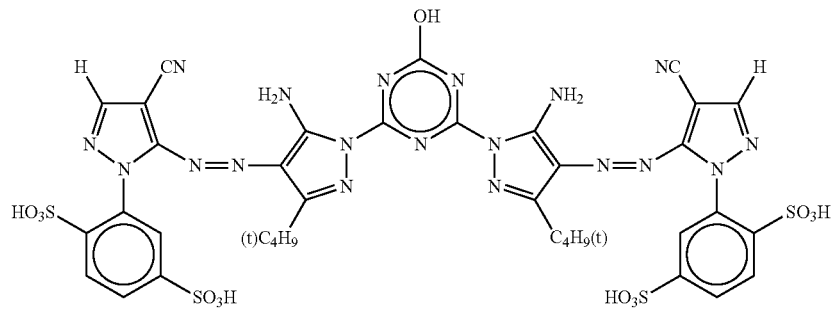
DYE-9
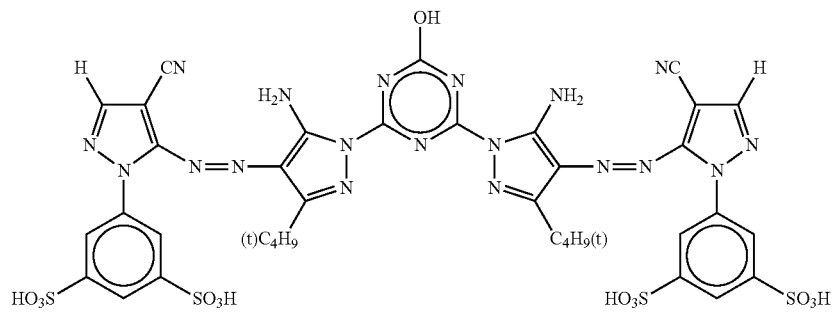
DYE-10
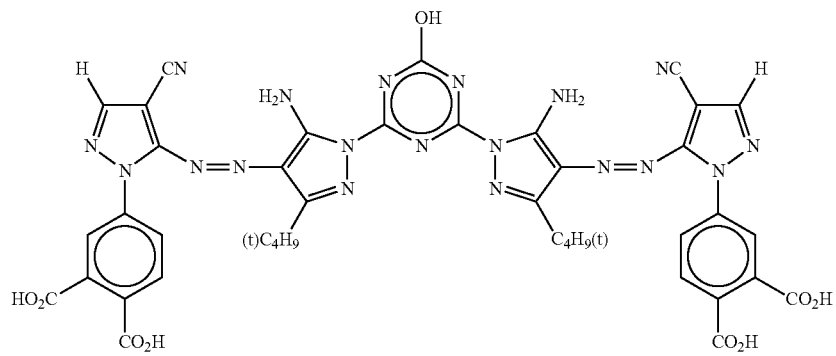
DYE-11
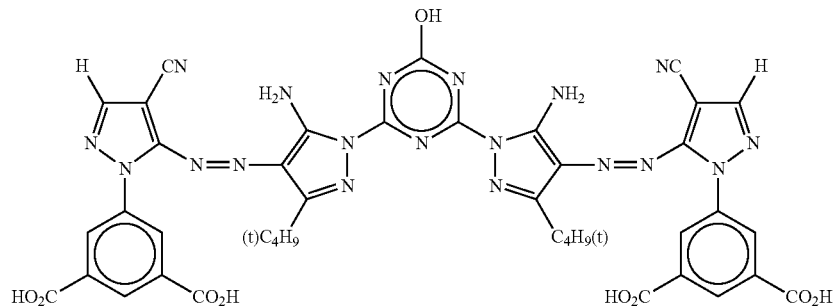

-continued
DYE-12
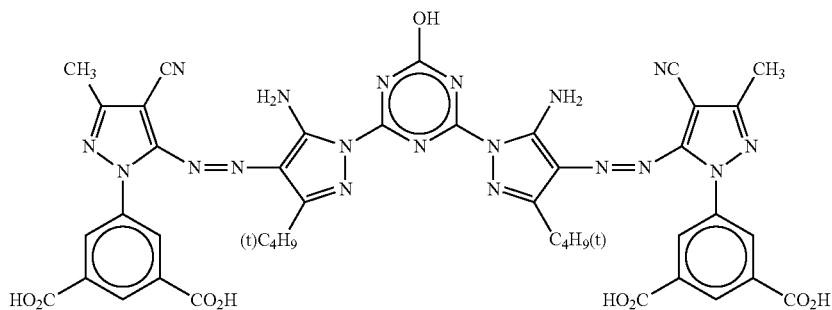
DYE-13
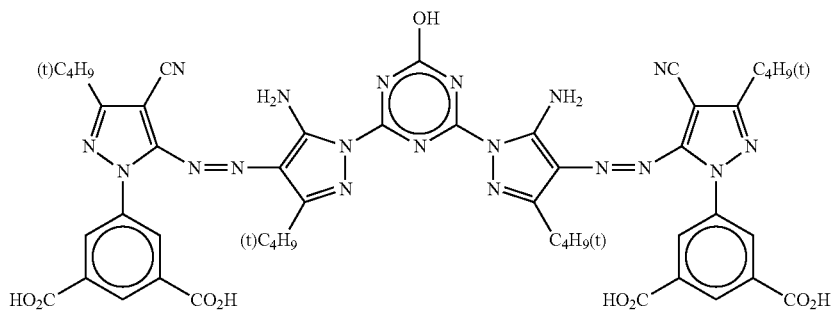
DYE-14
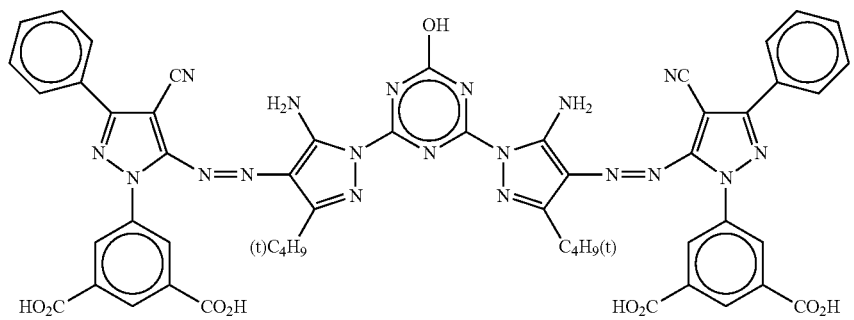
DYE-15
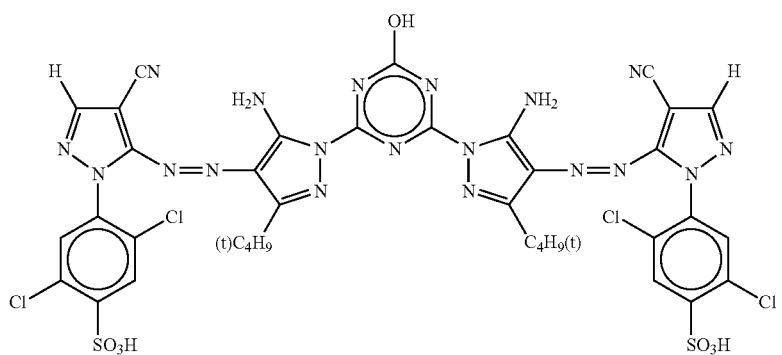
DYE-16
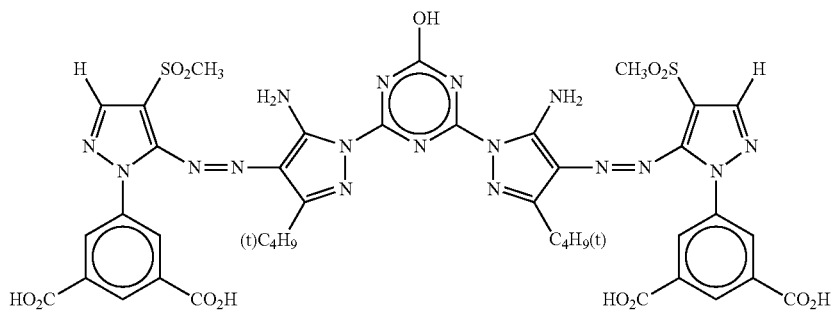

-continued
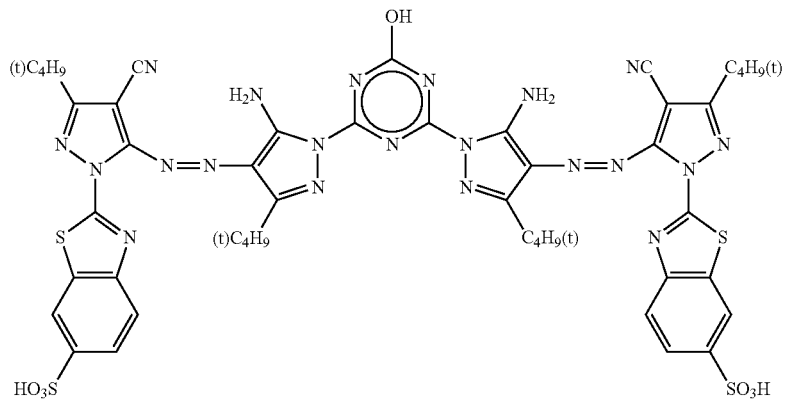
DYE-17
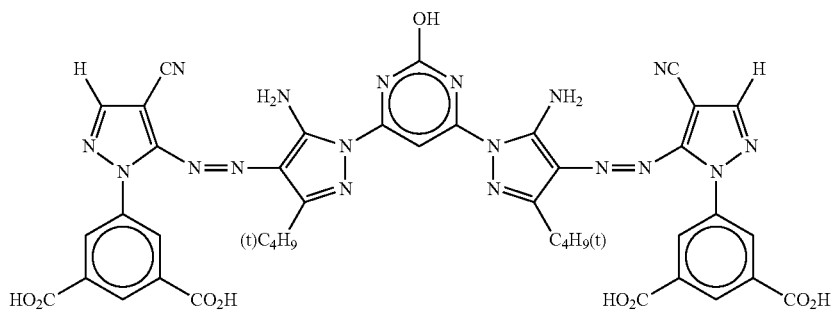
DYE-18
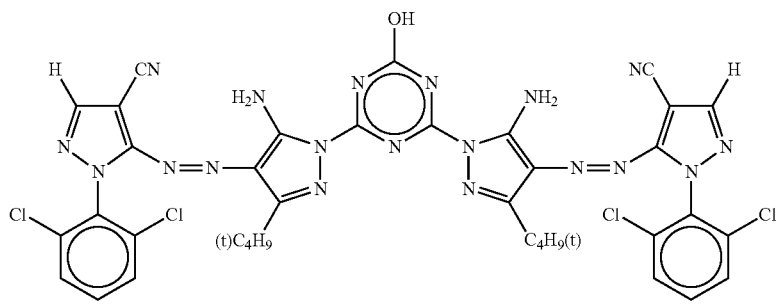
DYE-19
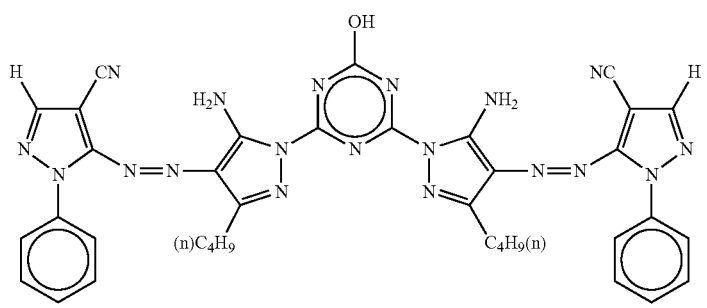
DYE-20
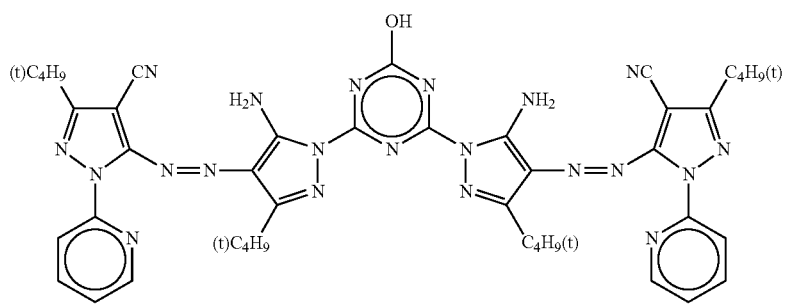
DYE-21

-continued
DYE-22
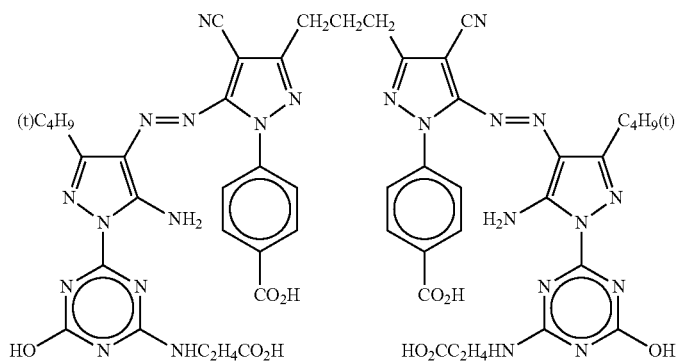
DYE-23
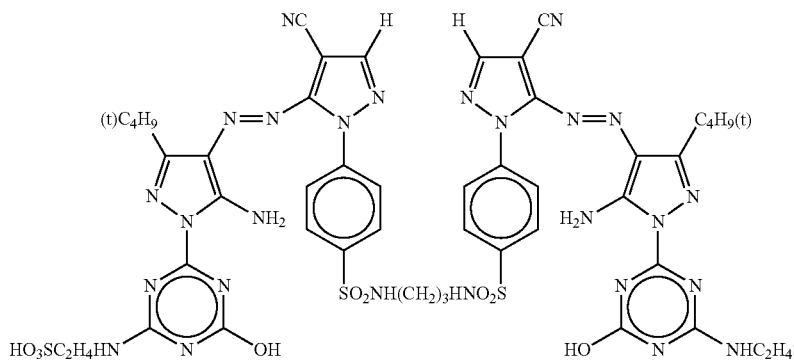
DYE-24
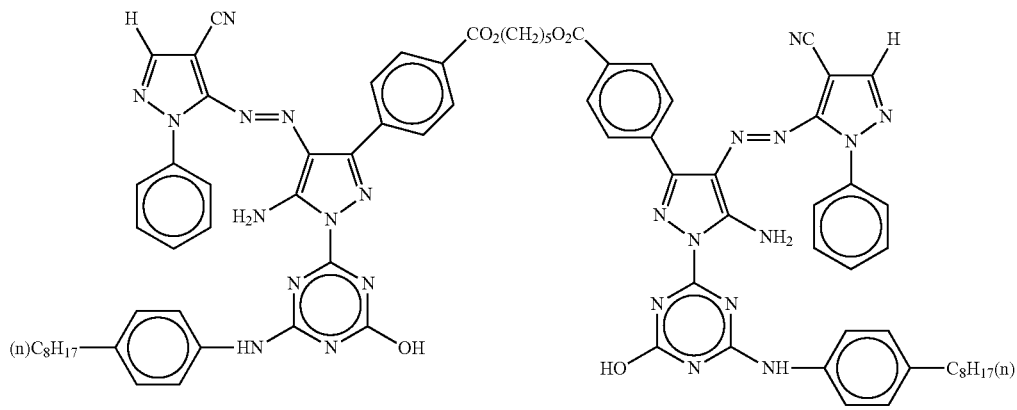
DYE-25
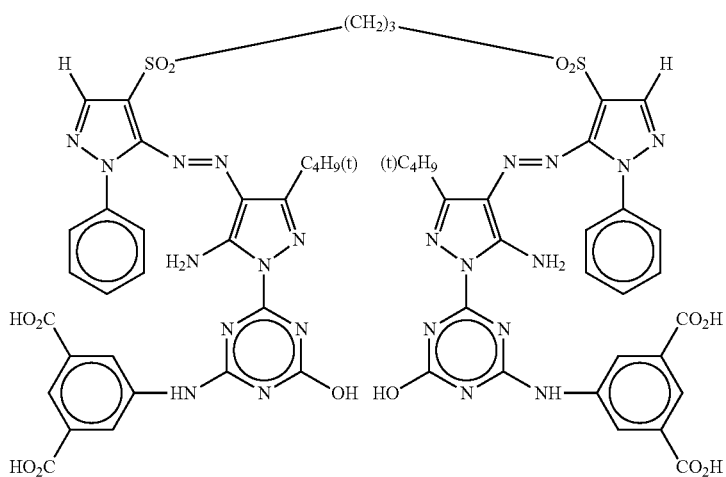

-continued

DYE-26

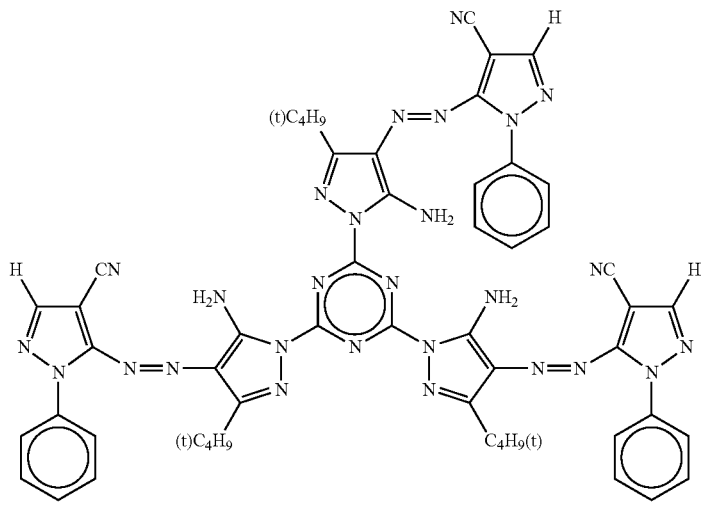

Then, the compound represented by the formula (7) in the invention will be described in details.

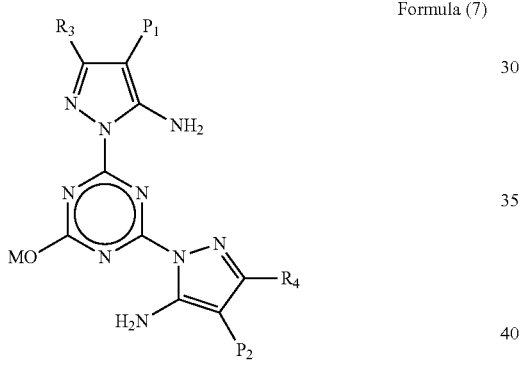

Formula (7)

The compounds represented by the formula (7) include a compound, and a salt thereof and a hydrate thereof.

The compounds represented by the formula (7) are useful novel compounds as organic photoconductive materials, light recording materials, or functional materials such as medicinals and agrochemicals other than dyes or pigments. Particularly, they are useful as synthetic intermediates for novel azo coloring matters/azomethine coloring matters.

In the formula (7), $R_3$ and $R_4$ are each independently the same as $R_1$ and $R_2$ represented by the formula (2), and the preferred examples thereof are also the same.

In the formula (7), $P_1$ and $P_2$ each independently represent a hydrogen atom or a leaving group.

In this specification, the leaving group denotes a group which leaves upon a chemical reaction. For example, it is a group which leaves upon the coupling reaction with diazonium salt, or a group which causes the addition elimination reaction of the oxidized of a phenylene diamine derivative with ease. Preferred examples of $P_1$ and $P_2$ may include a hydrogen atom, a halogen atom, an alkyloxy group, an aryloxy group, an alkyl thio group, or an aryl thio group. Out of these, a hydrogen atom or a halogen atom is preferred. Out of these, a hydrogen atom is preferable.

The methods for synthesizing the coloring matter or the intermediate of the invention will be described in details.

<1> Synthesis of Coupling Component

The coupling component (coloring matter intermediate which reacts with a diazonium salt, and derives therefrom an azo dyestuff) for use in synthesis of the coloring matter of the invention is preferably the compound represented by the following formula (8).

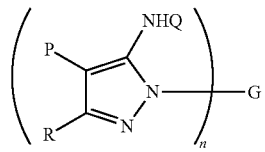

Formula (8)

R, G, and Q in the formula (8) are each independently the same as R, G, and Q in the formula (I), and the preferred examples thereof are also the same.

In the formula (8), n represents an integer of 1 to 3.

P represents a hydrogen atom or a leaving group. The leaving group denotes a group which leaves upon a chemical reaction. For example, it represents a group which leaves upon the coupling reaction with a diazonium salt, and a group which effects the addition elimination reaction with the oxidized product of a phenylene diamine derivative with ease. Preferred examples of P may include a hydrogen atom, a halogen atom, an alkyloxy group, aryloxy group, an alkyl thio group, or an aryl thio group. Out of these, a hydrogen atom or a halogen atom is preferred, and a hydrogen atom is most preferred.

Further preferred examples of the coupling component represented by the formula (8) are the compounds represented by the following formula (9), and salts or hydrates thereof.

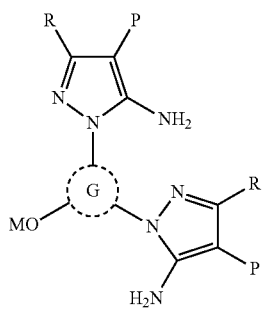

Formula (9)

In the formula (9), the substituents R, G, and P are respectively the same as R, G, and P in the formula (8), and preferred examples thereof are also the same. Incidentally, the compounds represented by the formula (7) are included in the compounds represented by the formula (9).

In the formula (9), M represents a hydrogen atom or a cation.

When M represents a cation, it is the same as M in the formula (1), and preferred examples thereof are also the same.

Particularly preferred examples of the coupling component represented by the formula (9) are the compounds represented by the following formula (10), or salts or hydrates thereof.

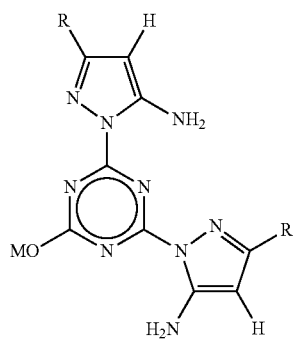

Formula (10)

In the formula (10), substituents R's are each independently the same as R's in the formula (8), and preferred examples thereof are also the same.

In the formula (10), M is the same as M in the formula (9), and preferred examples thereof are also the same.

Below, a method for synthesizing the coupling component represented by the formula (9) will be described.

The compound represented by the formula (9) can be obtained, for example, according to the following process.

Through a step (a) of allowing a base to act on a mixture of an organic compound (α) having a halogen atom eliminable with hydrazine and water, and a step (b) of mixing the reaction solution obtained in the step (a) and hydrazine, a hydrazine derivative is obtained. Then, from a step (c) of allowing the hydrazine derivative obtained in the step (b) to react with an acylacetonitrile compound in the presence of an acid and an organic solvent, the compound represented by the formula (9); (which is hereinafter referred to as a 5-aminopyrazole compound) is synthesized.

Examples of the organic compound (a) are cyanuric chloride, 2-chloropyrimidine, 3-chloropyridazine, 3,5-dichloropyridazine, 5-chloropyrazole, or 2-chloroimidazole. Preferred is cyanuric chloride, 3,5-dichloro pyridazine, or 2-chloroimidazole.

First, as the step (a), a base is allowed to act on a mixture of the organic compound (α) and water. In the invention, water can be used in this manner as a preferable reaction solvent for manufacturing a hydrazine derivative. The amount of water to be used based on the amount of the organic compound (α) is preferably 0.5 to 50 times by mass, and more preferably 1 to 20 times by mass.

In the invention, the organic compound (α) is preferably in a state dispersed in water. However, it can be in the form of an aqueous solution according to the type of the organic compound (α).

Whereas, the solvent for the mixture of the organic compound (α) and water mainly contains water as described above (10 to 100 mass %, and preferably 50 to 100 mass % based on the total amount of the solvent). However, if required, other solvents than water can be used. As such solvents, mention may be made of dimethylformamide, dimethylacetamide, dimethylsulfoxide, and the like.

The bases include inorganic bases and organic bases. As the inorganic bases, mention may be made of sodium hydroxide, lithium hydroxide, potassium hydroxide, sodium hydrogen carbonate, sodium carbonate, potassium carbonate, potassium acetate, sodium acetate, lithium acetate, and the like, preferred is sodium hydroxide, sodium hydrogen carbonate, or potassium carbonate. Further preferred is sodium hydrogen carbonate, or sodium hydroxide. As the organic bases, mention may be made of ammonia, hydrazine, triethylamine, diazo bicyclo undecene, pyridine, 2,6-dimethyl pyridine, dimethylaminopyridine, and the like. Preferred is ammonia, hydrazine, triethylamine, or pyridine. Further preferred is ammonia, or hydrazine. The amount of the base to be used is preferably 0.05 to 30.0 equivalents, and more preferably 0.5 to 15.0 equivalents based on the amount of the organic compound (α) to be used.

The reaction temperature is preferably 5° C. to 80° C., and more preferably 10° C. to 60° C.

The reaction time is preferably 30 minutes to 6 hours, and more preferably 1 hour to 3 hours.

Subsequently, as the step (b), the reaction solution obtained in the step (a) and hydrazine are mixed, and allowed to react with other, thereby to produce a hydrazine derivative. The mixing ratio of the organic compound (α) and hydrazine is, for example, preferably 1:1 to 1:20, and more preferably 1:2 to 1:10 in terms of the former:the latter (molar ratio).

The reaction temperature in the step (b) is preferably 0° C. to 90° C., more preferably 0° C. to 80° C., and further preferably 0° C. to 65° C. When it is less than 0° C., the reaction rate is remarkably slowed, and the length of time required for the synthesis becomes remarkably long. Therefore, this is uneconomical. Whereas, when the synthesis is carried out at a temperature as high as more than 90° C., the amount of by-products formed increases. Therefore this is not preferable.

The reaction time in the step (b) is preferably from 30 minutes to 300 minutes, more preferably from 30 minutes to 200 minutes, and further preferably 30 minutes to 150 minutes.

The reaction scheme when as the organic compound (α), cyanuric chloride is used, and as the base, sodium hydrogen carbonate is used will be shown below.

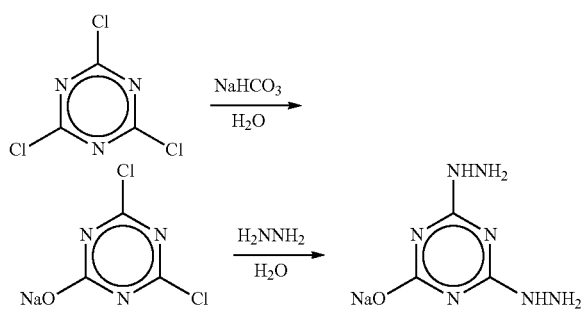

The hydrazine derivative can be allowed to react with an acylacetonitrile compound in the presence of an acid and an organic solvent, thereby to synthesize a 5-aminopyrazole compound.

This hydrazine derivative may be either the one produced according to this application, or the one produced according to other method than this application.

As the organic solvent, there is particularly demanded a solvent in which an intermediate including a hydrazine derivative and an acylacetonitrile compound added thereto (which is hereinafter simply referred to as an intermediate) is dissolved, and in which a 5-aminopyrazole compound is precipitated from the reaction system to suppress the formation of the reaction by-products.

In the invention, the organic solvent is a solvent which does not cause a liquid separation phenomenon during the reaction, and provides a uniform solution with the solvent. Examples thereof may include alcoholic organic solvents such as methanol, ethanol, propanol, isopropanol, butanol, t-butyl alcohol, and amyl alcohol, ketone type organic solvents such as acetone and methyl ethyl ketone, diol type organic solvents such as ethylene glycol, diethylene glycol, triethylene glycol, propylene glycol, dipropylene glycol, and 1,3-propanediol, ether type organic solvents such as ethylene glycol monomethyl ether, ethylene glycol monoethyl ether, and ethylene glycol diethyl ether, tetrahydrofuran, dioxane, and acetonitrile. These solvents may be used as a mixed solution of two or more thereof.

Preferred are the organic solvents with a polarity parameter (ET) value of 40 or more. Out of these, preferred are glycol type solvents having two or more hydroxyl groups in the solvent molecule, or alcoholic solvents having 3 or less carbon atoms, and preferably an alcohol solvents having 2 or less carbon atoms. Further, mixed solvents thereof are also included.

As organic solvents, especially, an organic solvent having a hydroxyl group is preferred. More preferred examples of alcohol may include methanol and ethanol. Further, glycols such as oligo- (particularly, di- and tri-), and poly-$C_2$ to $C_4$-alkylene glycols are also preferred. Whereas, ethylene-based compounds are also advantageous. Examples thereof may include ethylene glycol, 1,2-, and 1,3-propylene glycol, diethylene glycol, butylene glycol, di-, tri-, and tetra-ethylene glycol, di-, tri-, and tetra-propylene glycol, polyethylene- and polypropylene glycol, and glycerin.

More preferred examples may include methanol, ethylene glycol, diethylene glycol, triethylene glycol, polypropylene glycol, propylene glycol, dipropylene glycol, glycerin, a 1:2 (v/v) mixed solvent of ethylene glycol and diethylene glycol, a 3:1 (v/v) of propylene glycol and triethylene glycol, a 1:2 to 3 (v/v) of methanol and ethylene glycol, and a 1:2 to 5 (v/v) mixed solvent of methanol and triethylene glycol. The amount of the solvent to be used is 1 to 100 times by mass, preferably 1 to 50 times by mass, and further preferably 1 to 20 times by mass based on the amount of the compound represented by the formula (1).

The acid has no particular restriction. However, inorganic acids such as hydrochloric acid, phosphoric acid, sulfuric acid, and nitric acid, and organic acids such as methane sulfonic acid are also effective. The amount of the acid used is 1 to 100 times by mass, preferably 1 to 20 times by mass, and further preferably 1 to 10 times by mass based on the amount of the hydrazine derivative. When the amount of the acid is small, the solubility of the intermediate is inferior, and the reaction time becomes long. When the amount of the acid is too large, a large amount of by-products are formed, which may incur degradation in yield.

As the acyl groups in the acylacetonitrile compound, mention may be made of an acetyl group, a pivaloyl group, an isopropyl carbonyl group, a phenethyl carbonyl group, a 2-naphthyl carbonyl group, a 2-pyridyl carbonyl group, and the like. Particularly preferred is an acetyl group, a pivaloyl group, an isopropyl carbonyl group, or a phenethyl carbonyl group.

The acylacetonitrile compound is added in a ratio of preferably 1 to 5 mol, and more preferably 1 to 3 mol per mol of hydrazine of the hydrazine derivative.

The reaction temperature for the hydrazine derivative and the acylacetonitrile compound is preferably 0° C. to 120° C., more preferably 0° C. to 100° C., and further preferably 0° C. to 75° C.

The reaction time is preferably 1 hour to 20 hours, more preferably 1 hour to 15 hours, and further preferably 1 hour to 10 hours.

There will be shown below the reaction scheme of a series of steps of a method for producing a hydrazine derivative of the invention, and a method for producing a 5-aminopyrazole compound using the hydrazine derivative produced thereby. Incidentally, in the following scheme, there is shown the case where as the organic compound (α) of the starting material, cyanuric chloride; as the base, sodium hydrogen carbonate; as the acylacetonitrile compound, pivaloyl acetonitrile; as the acid, hydrochloric acid; and as the organic solvent, a mixed solvent of methanol and ethylene glycol are used. However, the invention is not limited thereto.

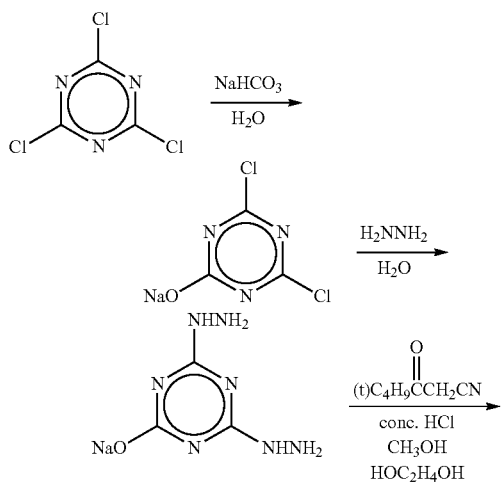

-continued

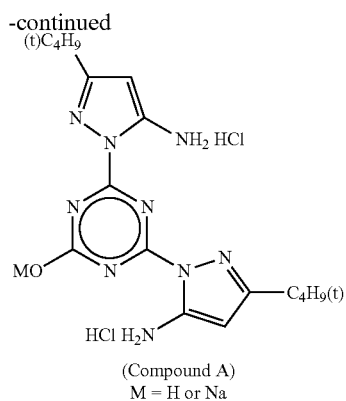

(Compound A)
M = H or Na

<2> Synthesis of Diazo Component:

The diazo component (coloring matter intermediate for deriving therefrom a diazonium salt) for use in synthesizing the coloring matter of the invention is preferably the compound represented by the following formula (11).

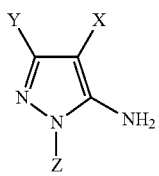

Formula (11)

The substituents X, Y, and Z in the formula (11) are the same as X, Y, and Z in the formula (I), respectively, and preferred examples thereof are also the same.

The compound represented by the formula (11) can be obtained, for example, in accordance with the following reaction formula. In the formula, R represents a lower alkyl group, and —OW represents a leaving group.

The diazonium salt preparation and coupling reaction can be carried out by conventional methods.

To the preparation of the diazonium salt of the formula (11), for example, there can be applied a conventional diazonium salt preparation method in which in an acid (e.g., hydrochloric acid, sulfuric acid, phosphoric acid, acetic acid, propionic acid, methane sulfonic acid, or trifluoromethane sulfonic acid)-containing reaction medium, a nitrosonium ion source such as nitrous acid, nitrite, or nitrosyl sulfuric acid is used.

As more preferred examples of the acids, mention may be made of the cases where acetic acid, propionic acid, methane sulfonic acid, phosphoric acid, and sulfuric acid are used alone or in combination. Out of these, particularly preferred are the system of use in combination of acetic acid and or propionic acid, and sulfuric acid.

As preferred examples of the reaction medium (solvent), use of organic acids or inorganic acids is preferable. Particularly, phosphoric acid, sulfuric acid, acetic acid, propionic acid, and methane sulfonic acid are preferred. Out of these, acetic acid and or propionic acid is preferred.

As a preferred example of the nitrosonium ion source, use of nitrosyl sulfuric acid in the preferred acid-containing reaction medium can prepare a diazonium salt with stability and with efficiency The amount of the solvent to be used based on the diazo component of the formula (11) is preferably 0.5 to 50 times by mass, more preferably 1 to 20 times by mass, and in particular preferably 3 to 10 times by mass.

In the invention, the diazo component of the formula (11) may be either in a state dispersed in water, or in the form of a dissolved solution according to the type of the diazo component.

The amount of the nitrosonium ion source to be used is preferably 0.95 to 5.0 equivalents, more preferably 1.00 to 3.00 equivalents, and in particular preferably 1.00 to 1.10 equivalents based on the amount of the diazo component.

The reaction temperature is preferably −15° C. to 30° C., more preferably −10° C. to 10° C., and further preferably −5°

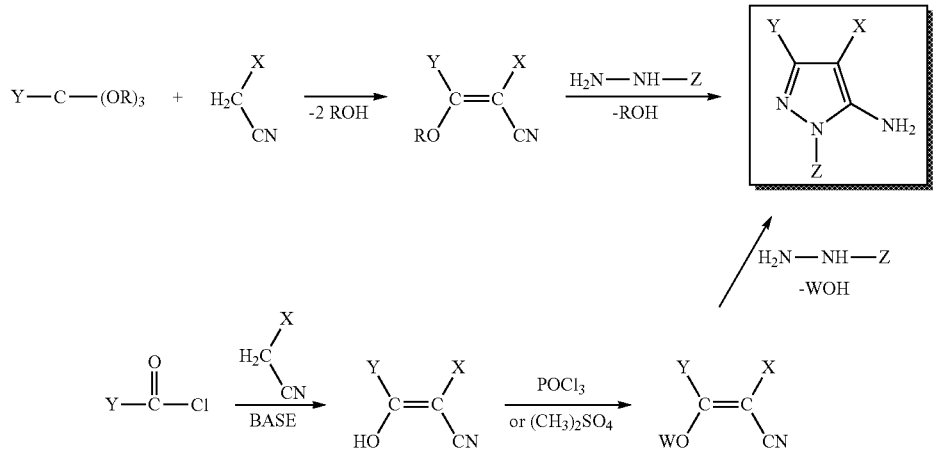

<3> Synthesis of Azo Coloring Matter of the Invention:

The coloring matter of the invention can be synthesized in the following manner. For example, the diazonium salt obtained by preparing the diazo component of the formula (11) with a known method is allowed to undergo an azo coupling reaction with the coupling component of the formula (8) or (9).

C. to 5° C. When it is less than −10° C., the reaction rate is remarkably slowed, and the length of time required for the synthesis becomes remarkably long. Therefore, this is uneconomical. Whereas, when the synthesis is carried out at a temperature as high as more than 30° C., the amount of by-products formed increases. Therefore this is not preferable.

The reaction time is preferably from 30 minutes to 300 minutes, more preferably from 30 minutes to 200 minutes, and further preferably 30 minutes to 150 minutes.

The coupling reaction (azo coloring matter preparation step) can be carried out in an acidic reaction medium to in a basic reaction medium. However, for the azo coloring matter of the invention, the reaction is preferably carried out in an acidic to neutral reaction medium. Particularly, carrying out of the reaction in an acidic reaction medium can suppress the decomposition of the diazonium salt, and can induce it to an azo coloring matter with efficiency.

As preferred examples of the reaction medium (solvent), organic acids, inorganic acids, or organic solvents can be used. However, particularly, organic solvents are preferred, and a solvent is preferred which does not cause a liquid separation phenomenon during the reaction, and provides a uniform solution with the solvent. Examples thereof may include alcoholic organic solvents such as methanol, ethanol, propanol, isopropanol, butanol, t-butyl alcohol, and amyl alcohol, ketone type organic solvents such as acetone and methyl ethyl ketone, diol type organic solvents such as ethylene glycol, diethylene glycol, triethylene glycol, propylene glycol, dipropylene glycol, and 1,3-propanediol, ether type organic solvents such as ethylene glycol monomethyl ether, ethylene glycol monoethyl ether, and ethylene glycol diethyl ether, tetrahydrofuran, dioxane, and acetonitrile. These solvents may be used as a mixed solution of two or more thereof.

Preferred are the organic solvents with a polarity parameter (ET) value of 40 or more. Out of these, preferred are glycol type solvents having two or more hydroxyl groups in the solvent molecule, or alcoholic solvents having 3 or less carbon atoms, and preferably an alcohol solvent having 2 or less carbon atoms (e.g., methanol, or ethanol). Further, mixed solvents thereof are also included.

The amount of the solvent to be used is preferably 1 to 100 times by mass, more preferably 1 to 50 times by mass, and further preferably 2 to 10 times by mass based on the amount of the coupling component represented by the formula (8) or (9).

In the invention, the coupling component represented by the formula (8) or (9) may be either in a state dispersed in a solvent, or in the form of a dissolved solution according to the type of the coupling component.

As for the amount of the coupling component to be used, the azo component is preferably 0.95 to 5.0 equivalents, more preferably 1.00 to 3.00 equivalents, and in particular preferably 1.00 to 1.50 equivalents based on the amount of the azo coupling moiety.

The reaction temperature is preferably −30° C. to 30° C., more preferably −15° C. to 10° C., and further preferably −10° C. to 5° C. When it is less than −30° C., the reaction rate is remarkably slowed, and the length of time required for the synthesis becomes remarkably long. Therefore, this is uneconomical. Whereas, when the synthesis is carried out at a temperature as high as more than 30° C., the amount of by-products formed increases. Therefore this is not preferable.

The reaction time is preferably from 30 minutes to 300 minutes, more preferably from 30 minutes to 200 minutes, and further preferably 30 minutes to 150 minutes.

In the method for synthesizing an azo coloring matter of the invention, the product (azo coloring matter) obtained by these reactions can be made available with purification or without purification after having been treated according to a common post-treatment method of an organic synthesis reaction.

Namely, for example, the one freed from the reaction system can be made available without purification, or by carrying out purification operations by recrystallization, salt formation, column chromatography (e.g., gel permeation chromatography (SEPHADEX™ LH-20: manufactured by Pharmacia), and the like alone or in combination.

Alternatively, after the completion of the reaction, the reaction solvent is distilled away, or is not distilled away, and the product is poured into water or ice, followed by neutralization, or not followed by neutralization. The thus freed one can also be made available without purification, or after carrying out purification operations by recrystallization, salt formation, column chromatography, and the like alone or in combination.

Further alternatively, after the completion of the reaction, the reaction solvent is distilled away, or is not distilled away, and the product is poured into water or ice, followed by neutralization, or not followed by neutralization. The one extracted with an organic solvent/aqueous solution can also be made available without purification, or after carrying out purification operations by recrystallization, salt formation, column chromatography, and the like alone or in combination.

As the uses of the coloring matter of the invention, mention may be made of image recording materials for forming images, particularly, color images. Specifically, mention may be made of recording materials for ink jet system described below in details, and in addition, heat sensitive recording materials, pressure sensitive recording materials, recording materials using an electrophotographic system, transfer type silver halide light sensitive materials, printing inks, recording pens, and the like. Preferably, mention may be made of recording materials for ink jet system, heat sensitive transfer type recording materials, and recording materials using an electrophotographic system. Further preferably, mention may be made of recording materials for ink jet system.

Whereas, the compounds are also applicable to color filters for recording/reproducing color images for use in solid-state image pickup devices such as CCDs, and displays such as LCDs and PDPs, and dyeing solutions for dyeing various fibers.

The coloring matter of the invention are used by having been adjusted in physical properties such as solubility, dispersibility, and thermal transfer property suitable for the intended use by substituents. Further, the coloring matters of the invention are also usable in dissolved state, in emulsion dispersed state, and further in solid dispersion state according to the system used.

[Ink]

The ink of the invention denotes an ink containing at least one coloring matter of the invention.

The ink of the invention can contain medium. It is particularly suitable as ink for ink jet recording when a solvent is used as the medium. The ink of the invention can be manufactured by using an oleophilic medium or an aqueous medium as the medium, and dissolving and/or dispersing the coloring matter of the invention therein. Preferred is the case where an aqueous medium is used. The ink of the invention includes a composition for ink exclusive of the medium. If required, other additives may be contained in the ink of the invention in such a range not to impair the effects of the invention. Examples of other additives may include known additives such as an anti-drying agent (wetting agent), an antifading agent, an emulsion stabilizer, a penetration accelerator, a UV absorber, an antiseptic agent, an antifungal agent, a pH adjuster, a surface tension regulator, an antifoaming agent, a viscosity modifier, a dispersant, a dispersion stabilizer, a rust inhibitor, and a chelating agent (described in JP-A-2003-306623). These various additives are directly added to an ink solution for a water soluble ink. When an oleophilic dye is used in the form of a dispersion, generally, it is added to the dispersion after preparation of a dye dispersion. However, it may be added to an oil phase or a water phase for the preparation.

When the coloring matter of the invention is dispersed in an aqueous medium, preferably, as in JP-A-11-286637, JP-A-2001-240763 (Japanese Patent Application No. 2000-78491), JP-A-2001-262039 (Japanese Patent Application No. 2000-80259), and JP-A-2001-247788 (Japanese Patent Application No. 2000-62370), colored fine particles containing a coloring matter and an oil soluble polymer are dispersed in an aqueous medium, or as in JP-A-2001-262018 (Japanese Patent Application No. 2000-78454), JP-A-2001-240763 (Japanese Patent Application No. 2000-78491), and JP-A-2001-335734 (JP-A-2000-203856), the coloring matter of the invention dissolved in a high boiling point organic solvent is dispersed in an aqueous medium. As the specific method for dispersing the coloring matter of the invention in an aqueous medium, the oil soluble polymer, the high boiling point organic solvent, and additives, to be used, and the amount of the materials used, those described in the foregoing patent publications may be preferably used. Alternatively, the azo coloring matter may also be dispersed in the form of fine particles still in solid form. For dispersion, a dispersant or a surfactant is usable.

As the dispersing devices, there can be used a simple stirrer or impeller stirring system, an in-line stirring system, a mill system (such as a colloid mill, a ball mill, a sand mill, an attritor, a roll mill, or an agitator mill), an ultrasonic system, a high-pressure emulsifying and dispersing system (high-pressure homogenizer; as specific commercially available devices, Gaulin Homogenizer, Microfluidizer, DeBEE2000, and the like). The details of the method for preparing the ink jet recording ink are described in, other than the foregoing patent publications, respective publications of JP-A-5-148436, JP-A-5-295312, JP-A-7-97541, JP-A-7-82515, JP-A-7-118584, JP-A-11-286637, JP-A-2001-2271003 (Japanese Patent Application No. 2000-87539), which is also usable for the preparation of the ink jet recording ink of the invention.

As the aqueous medium, a mixture containing water as a main component, and if desired, containing a water-miscible organic solvent added therein can be used. As the examples of the water-miscible organic solvent, those described in JP-A-2003-306623 are usable. Incidentally, the water-miscible organic solvents may also be used in combination of two or more thereof.

The coloring matter of the invention is preferably contained in an amount of 0.1 part by mass or more and 20 parts by mass or less, more preferably contained in an amount of 0.2 part by mass or more and 10 parts by mass or less, and further preferably contained in an amount of 0.5 to 9 parts by mass per 100 parts by mass of the ink jet recording ink of the invention. Further, the ink for ink jet of the invention, other coloring matters may be used in combination with the coloring matter of the invention. When two or more coloring matters are used in combination, the total amount of the coloring matters contained preferably falls within the foregoing range.

The ink of the invention may be used not only for the formation of a monochrome image but also for the formation of a full color image. For the formation of a full color image, a magenta tone ink, a cyan tone ink, and a yellow tone ink can be used. Further, for adjusting the tone, a black tone ink may further be used.

Further, the ink for ink jet recording of the invention can use, other than the coloring matter in the invention, other yellow dyes at the same time. As the applicable yellow dyes, the applicable magenta dyes, and the applicable cyan dyes, given ones can be used, respectively. However, respective dyes described in paragraph Nos. 0090 to 0092 of JP-A-2003-306623 are usable. As the applicable black materials, mention may be made of, other than disazo, trisazo, and tetraazo dyes, a dispersion of carbon black.

[Ink Jet Recording Method]

The ink jet recording method of the invention provides energy to the ink jet recording ink, and forms images on known image receiving materials, i.e., ordinary paper and resin-coated paper, such as ink jet-specific paper, film, electrophotographic common paper, cloth, glass, metal, ceramic, or the like described in JP-A-8-169172, JP-A-8-27693, JP-A-2-276670, JP-A-7-276789, JP-A-9-323475, JP-A-62-238783, JP-A-10-153989, JP-A-10-217473, JP-A-10-235995, JP-A-10-337947, JP-A-10-217597, and JP-A-10-337947. Incidentally, as the ink jet recording method of the invention, the description of paragraph Nos. 0093 to 0105 of JP-A-2003-306623 is applicable.

For the formation of an image, a polymer latex compound may be used in combination for the purpose of imparting the glossiness or the water resistance, or improving the weatherability. The timing of imparting the polymer latex to the image receiving material may be before or after imparting the colorant or simultaneously with it. Accordingly, the receiving site may be in the image receiving paper or in the ink. Alternatively, the polymer latex may be used in the form of a liquid material of the polymer latex alone. Specifically, the methods described in JP-A-2002-166638 (Japanese Patent Application No. 2000-363090), JP-A-2002-121440 (Japanese Patent Application No. 2000-315231), JP-A-2002-154201 (Japanese Patent Application No. 2000-354380), JP-A-2002-144696 (Japanese Patent Application No. 2000-343944), JP-A-080759 (Japanese Patent Application No. 2000-268952), and Japanese Patent Application Nos. 2000-299465 and 2000-297365 may be preferably used.

[Color Toner]

The content of the coloring matter of the invention per 100 parts by mass of the color toner of the invention has no particular restriction. However, it is preferably 0.1 part by mass or more, more preferably 1 to 20 parts by mass, and most preferably 2 to 10 parts by mass.

As the color toner binder resins for introducing the coloring matter of the invention, all the commonly used binders are usable. For example, styrene type resins, acrylic type resins, styrene/acrylic type resins, and polyester resins may be mentioned.

To the toner, inorganic fine powder and organic fine particles may be externally added for the purposes of improving the fluidity, controlling the electric charge, or other purposes. Silica fine particles or titania fine particles, surface-treated with a coupling agent containing an alkyl group are preferably used. Incidentally, these preferably have a number average primary particle diameter of 10 to 500 nm, and preferably are added into the toner in an amount of 0.1 to 20 mass %.

All the release agents which have been conventionally used may be used as the release agents. Specifically, mention may be made of olefins such as low-molecular-weight polypropylenes, low-molecular-weight polyethylenes, and ethylene/propylene copolymers; microcrystalline wax, carnauba wax, sazol wax, paraffin wax, and the like. These are each preferably added into the toner in an amount of 1 to 5 mass %.

The charge control agent may be added, if required. They are preferably achromatic from the viewpoint of color-forming property. Examples thereof may include those having a quaternary ammonium salt structure or a calyx allene structure.

The carrier to be used may be either an uncoated carrier composed of only magnetic material particles of iron, ferrite, or the like, or a resin-coated carrier obtained by coating the surface of a magnetic material particle with a resin or the like. The average particle diameter of this carrier is preferably 30 to 150 μm in terms of volume average particle diameter.

The method for forming an image, to which the toner of the invention is applicable, has no particular restriction. Examples of the method may include a method in which color images are repeatedly formed on a photosensitive material, and then transferred, to form an image; and a method in which images formed on a photosensitive material are transferred to an intermediate transfer material and the like sequentially, then a color image is formed on the intermediate transfer material or the like, and then is transferred to an image-forming member such as paper, to form a color image.

[Heat Sensitive Recording (Transfer) Material]

The heat sensitive recording material is formed of an ink sheet including the coloring matter of the invention coated on a support together with a binder, and an image receiving sheet which fixes the coloring matter transferred in accordance with a heat energy applied from a thermal head in response to an image recording signal. The ink sheet can be formed in the following manner. The compound of the invention is dissolved in a solvent with a binder. Alternatively, it is dispersed in the form of fine particles in a solvent. As a result, an ink solution is prepared, and the ink is coated on a support, and appropriately dried. The amount of the ink to be coated on the support has no particular restriction. However, it is preferably 30 to 1000 mg/m$^2$. As the preferred binder resins, ink solvents, supports, and further image receiving sheets, those described in JP-A-7-137466 can be preferably used.

In order to apply the heat sensitive recording material to a heat sensitive recording material capable of full color image recording, preferably a cyan ink sheet containing a heat diffusible cyan coloring matter capable of forming a cyan image, a magenta ink sheet containing a heat diffusible magenta coloring matter capable of forming a magenta image, and a yellow ink sheet containing a heat diffusible yellow coloring matter capable of forming a yellow image are sequentially coated on a support for the formation. Alternatively, if required, another ink sheet containing a black image forming material may be further formed.

[Color Filter]

As the methods for forming a color filter, there is a method in which first, a pattern is formed with a photoresist, followed by dyeing, or a method in which as disclosed in JP-A-4-163552, JP-A-4-128703, and JP-A-4-175753, a pattern is formed by a photoresist to which a coloring matter has been added. As the methods used for introducing the coloring matter of the invention into a color filter, any of these methods may be used. As the preferred method, mention may be made of the following method for forming a color filter as described in JP-A-4-175753 or JP-A-6-35182. A positive type resist composition containing a thermosetting resin, a quinonediazide compound, a crosslinking agent, a colorant, and a solvent is coated on a substrate. Then, it is exposed to light through a mask to develop the exposed area. As a result, a positive type resist pattern is formed, and the entire surface of the positive type resist pattern is exposed to light. Then, the positive type resist pattern after exposure is hardened. Alternatively, according to an ordinary method, a black matrix is formed, which can provide a R, G, and B primary color type or Y, M, and C complementary color type color filter. Also for the color filter, the amount of the coloring matter to be used has no particular restriction. However, it is preferably 0.1 to 50 mass %.

As the thermosetting resin, quinonediazide compound, crosslinking agent, and solvent, for use in this step, and the amounts thereof, those described in the foregoing patent documents may be preferably used.

EXAMPLES

Below, the invention will be described by way of examples. However, the invention is by no way limited thereto.

Example 1

As the typical example, a method for synthesizing a coloring matter (DYE-11) will be described.

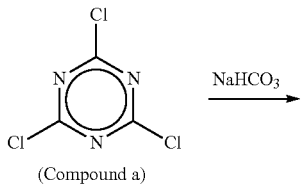

(Compound a)

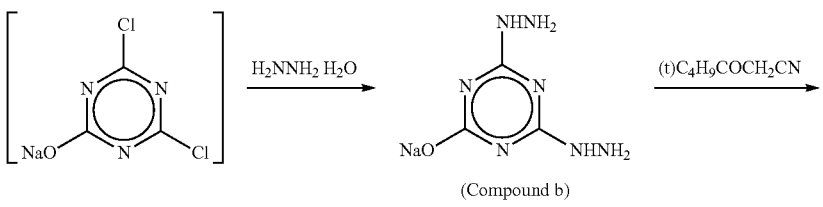

(Compound b)

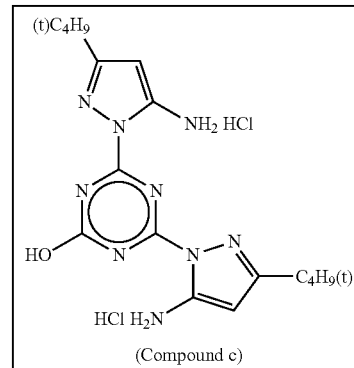

(Compound c)

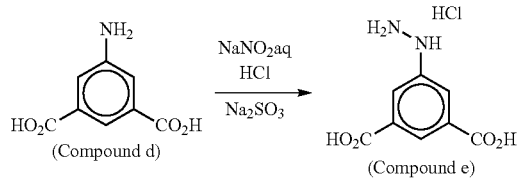 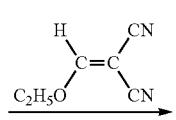 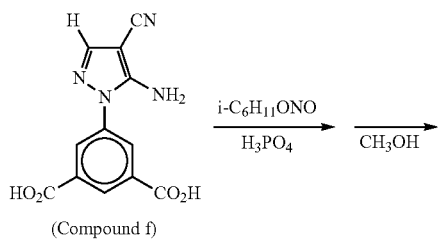

(DYE-11)

(1) Synthesis of Compound b:

25.5 g of sodium hydrogen carbonate and 150 mL of ion exchange water were heated to 40° C. 25.0 g of cyanuric chloride (product from Tokyo Chemical Industry Co., Ltd.) was divided into 5 portions and added thereto every 10 minutes, and stirred for 1 hour. The solution was added dropwise to a mixed solution (8° C.) of 52.8 mL of hydrazine and 47 mL of ion exchange water so that the internal temperature does not exceed 10° C. The internal temperature was increased up to 50° C., and stirring was carried out for 30 minutes. The precipitated crystal was filtrated, thereby to obtain 23.4 g of compound b (hydrazine derivative: m.p.>300° C.). The yield was 94.7%.

(2) Synthesis of Compound c:

35.0 g of the compound b (hydrazine derivative) was suspended in 420 mL of ethylene glycol, and stirred at an internal temperature of 50° C. 59 mL of concentrated hydrochloric acid and subsequently 60.1 g of pivaloyl acetonitrile (product from Tokyo Chemical Industry Co., Ltd.) were added, and stirred at 50° C. for 10 hours. 95 mL of concentrated hydrochloric acid and 145 mL of methanol were additionally added, and stirring was further carried out for 8 hours. The solution was cooled to room temperature, and then, the precipitated crystal was filtrated away, thereby to obtain 81.6 g of a compound c (5-aminopyrazole derivative: m.p.=233 to 235° C.). The yield was 94.2%. $^1$H-NMR (DMSO-d6), δ value TMS standard: 1.2 to 1.3 (18H, s))

(3) Synthesis of Compound e:

90.57 g of a compound d (product from Tokyo Chemical Industry Co., Ltd.) was suspended in 500 ml of $H_2O$, and 130 ml of concentrated hydrochloric acid was poured. Then, the solution was cooled until the internal temperature became 5° C. or less. Then, 36.23 g of sodium nitrite and 70 ml of an aqueous solution were added dropwise thereto at an internal temperature in the range of 4 to 6° C. Further, stirring was carried out at an internal temperature of 5° C. or less for 30 minutes. Then, 159 g of sodium sulfite and 636 ml of $H_2O$ were poured while keeping the internal temperature at 20° C. or less. Further, at an internal temperature of 25° C., 250 ml of concentrated hydrochloric acid was poured. Subsequently, stirring was carried out at an internal temperature 90° C. for 1 hour. Then, the internal temperature was cooled to room temperature, followed by filtration, washing with 200 ml of water, and air drying. Then, 80.0 g of a compound e was obtained.

(4) Synthesis of Compound f:

To 209 ml of an ethanol suspension of 23.3 g of the compound e, 28 ml of triethylamine was added dropwise at room temperature. Then, 12.2 g of ethoxy methylene malononitrile (ALDRICH product) was divided and added thereto. The solution was refluxed for 3 hours, cooled down to room temperature, followed by filtration, and washed with 400 ml of isopropyl alcohol, and dried. Then, 23.57 g of a compound f was obtained.

(5) Synthesis of DYE-11:

At an internal temperature of 4° C. or less, to 32.4 mL of sulfuric acid, 145.56 mL of acetic acid was poured. Subsequently, with stirring at an internal temperature 7° C. or less, 15.9 mL 40% nitrosyl sulfuric acid (ALDRICH product) was added dropwise thereto.

32.4 g of a compound f was divided and added, and with stirring at an internal temperature 10° C., stirring was carried out at the same temperature for 60 minutes. Then, 1.83 g of urea was added into the reaction mixture. To a solution obtained by suspending 18.8 g of the compound C in 470 ml of methanol, diazonium salt was added dropwise at an internal temperature of less than 0° C. Stirring was carried out still at the same temperature for 30 minutes. Then, the internal temperature of the reaction solution was increased up to room temperature, followed by filtration, washing with methanol, and washing with $H_2O$, resulting in a coarse crystal. Subsequently, the coarse crystal was suspended in 400 ml of methanol, and the suspension was stirred under reflux for 1 hour. Then, the suspension was cooled down to room temperature, followed by filtration, washing with methanol, washing with water, and washing with methanol. Then, drying was carried out at 75° C. overnight. Then, 34.4 g of free acid type crystal of DYE-11 was obtained. The obtained crystal was prepared into a 10 wt % aq (at 25° C.: pH nearly equal to 8.3: KOH aq preparation). Then, at an internal temperature of 50° C., IPA was added, and crystallized, followed by cooling, filtration, washing with IPA, and drying. Then, 35 g of DYE-11 (potassium salt) was obtained.

λmax=436.4 nm ($H_2O$), ε: 3.53×10$^4$ (dm$^3$.cm/mol)

Example 2

Below, synthesis examples of the coloring matter of the invention will be shown. Other coloring matters can be synthesized in the same manner by applying the synthesis method of the coloring matter (DYE-11). The λmax in $H_2O$ and the δ value of each synthesized coloring matter are shown in Table 1.

TABLE 1

| DYE-No. | λmax ($H_2O$) | ε ($H_2O$) |
|---|---|---|
| DYE-8 | 444.6 nm | 3.76 × 10$^4$ |
| DYE-9 | 442.6 nm | 3.44 × 10$^4$ |
| DYE-11 | 436.4 nm | 3.53 × 10$^4$ |
| DYE-12 | 434.3 nm | 3.50 × 10$^4$ |
| DYE-13 | 449.0 nm | 3.66 × 10$^4$ |
| DYE-14 | 435.0 nm | 3.60 × 10$^4$ |
| DYE-15 | 437.0 nm | 3.54 × 10$^4$ |

Example 3

To the following components, ultrapure water (resistance value 18 MΩ or more) was added to a total volume of 1 liter. Then, stirring was carried out for 1 hour while heating at 50 to 60° C. Then, the solution was vacuum filtrated through a micro filter with an average pore diameter of 0.25 µm, thereby to prepare a yellow ink solution Y-101.

[Formulation of Yellow Ink Y-101]

| (Solid contents) | |
|---|---|
| Yellow dye of the invention (DYE-11) | 50 g/l |
| Proxel (manufactured by Avecia) | 5 g/l |
| Urea | 10 g/l |
| (Liquid components) | |
| Triethylene glycol monobutyl ether (DGB) | 101 g/l |
| Glycerin (GR) | 118 g/l |
| Triethylene glycol (DEG) | 95 g/l |
| 2-Pyrrolidone | 20 g/l |

-continued

| | |
|---|---|
| Triethanolamine (TEA) | 10 g/l |
| Surfynol 465 (SW) (manufactured by Air Products) | 10 g/l |

Ink solutions Y-102 to 105 were manufactured in the same manner as with the preparation of the ink solution Y-101, except that the coloring matter was changed as shown in Table 2 shown below.

At this step, an ink solution 101 was formed by using a comparative coloring matter a in Table 2 as an ink solution for comparison.

Comparative Coloring Matter a

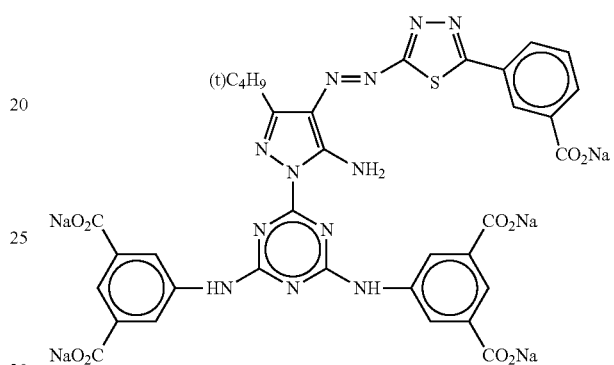

When the coloring matter was changed, it was used such that the amount of the coloring matter added is equimolar to that of the ink solution Y-101.

Whereas, as the comparative type of the ink, PM-G800 yellow ink cartridge manufactured by EPSON CORPORATION was used.

Incidentally, in Table 2, "discharge stability", "light fastness property", "heat fastness property", "ozone (gas) resistance", "metal gloss", "chromaticity", and "solution stability" were rated in the following manner. Each ink was charged in the cartridge of yellow ink of an ink jet printer PM-G800 manufactured by EPSON Corp. For other color inks, inks of PMG800 were used. For the image receiving sheets, EPSON photo paper sheets <gloss>, and EPSON photo paper sheets CRISPIA <high gloss> were used. Thereon, yellow monochrome image patterns, and green, red, and gray image patterns were printed with stepwise changing densities. Thus, the image quality, and the ink discharge property and image fastness property were evaluated.

For the inks for ink jet of the Examples (ink solutions Y101, 102, 103, 104, and 105) and Comparative Examples (ink solutions 101 and PM-G800 yellow ink), the following evaluations were carried out. The results are shown in Table 2.

(Evaluation Experiment)

1) For the discharge stability, a cartridge was set in a printer, and discharge of ink from all the nozzles was checked. Then, 20 A4 size paper sheets were outputted, and rated based on the following criteria.

A: No irregular printing from the start of printing till the completion;

B: Output with irregular printing occurs; and

C: Irregular printing occurs from the start of printing till the completion

2) As for the image storability of the yellow coloring matter, the following evaluations were carried out using printing samples.

[1] As for the light fastness property, the image density immediately after printing was measured by means of X-rite 310. Then, by means of a weather meter manufactured by Atlas Co., the image was irradiated with xenon light (100000 lx) for 14 days. Then, the image density Cf was measured again to determine the dye residual ratio Cf/Ci×100. Thus, the evaluation was carried out. As for the dye residual ratio, the evaluations were carried out at 3 points with reflection densities of 1, 1.5, and 2.

The case where the dye residual ratios at all densities were 80% or more was rated as A; the case where the ratios at two points were less than 80% was rated as B; and the case where the ratios at all the densities were less than 80% was rated as C.

[2] As for the heat fastness property, a sample was stored for 7 days under the conditions of 80° C. and 60% RH. Then, the densities before and after storage were measured by means of X-Rite 310 to determine the dye residual ratio. Thus, the evaluation was carried out. As for the dye residual ratio, the evaluations were carried out at 3 points with reflection densities of 1, 1.5, and 2. The case where the dye residual ratios at all densities were 95% or more was rated as A; the case where the ratios at two points were less than 95% was rated as B; and the case where the ratios at all the densities were less than 95% was rated as C.

[3] As for the ozone resistance, a sample was allowed to stand in a box with an ozone gas concentration set at 5 ppm for 14 days. Then, the image densities before and after standing under an ozone gas were measured by means of a reflection densitometer (X-Rite 310TR). Thus, evaluation was carried out as the dye residual ratio. Incidentally, the measurements were carried out at 3 points with the reflection densities of 1, 1.5, and 2.0. The ozone gas concentration in the box was set by means of an ozone gas monitor (model: OZG-EM-01) manufactured by APPLICS.

The case where the dye residual ratios at all densities were 80% or more was rated as A; the case where the ratios at one or two points were less than 80% was rated as B; and the case where the ratios at all the densities were less than 70% was rated as C. Thus, rating was conducted on a scale of three levels.

3) Occurrence or non-occurrence of metal gloss: The yellow, and green and red solid printed image portions were visually observed by reflected light, and evaluated.

4) Chromaticity: A yellow monochrome image pattern with a stepwise changing density was measured for CIE L*a*b* by Spectro Eye manufactured by Gretag Macbeth. The a* and the b* at a reflection density of 1.0 are shown in Table below.

5) Solution stability: A 10 mass % aqueous solution of each dye was allowed to stand at 60° C. for 10 days. Then, the absorbance was measured, and the change ratio with respect to the room temperature (23° C.) is shown in Table below.

TABLE 2

| Ink | Discharge stability | [1] Light fastness property | [2] Heat fastness property | [3] Ozone fastness property | Metal gloss | Chromaticity a* | Chromaticity b* | Solution stability | Coloring matter No. |
|---|---|---|---|---|---|---|---|---|---|
| Y101 | A | A | A | A | Occurrence | −9.7 | 87.5 | 99.8 | DYE-11 |
| Y102 | A | A | A | A | Occurrence | −8.0 | 84.8 | 99.7 | DYE-12 |
| Y103 | A | A | A | A | Occurrence | −13.4 | 78.9 | 99.7 | DYE-8 |
| Y104 | A | A | A | A | Occurrence | −10.5 | 80.3 | 99.8 | DYE-9 |
| Y105 | A | A | A | A | Occurrence | −9.9 | 90.2 | 99.7 | DYE-13 |
| 101 | A | B | A | B | Non-Occurrence | −6.3 | 82.1 | 49.8 | Comparative coloring matter a |
| PM-G800 | A | C | B | C | Occurrence | −7.6 | 74.8 | 99.9 | — |

The results of the table indicate as follows. With the system using the ink of the invention, the discharge property and the weatherability are excellent, and the occurrence of metal gloss is suppressed. The hue as yellow is excellent (a* is minus=less reddish, and b* is large=high color saturation), and the solution stability is excellent.

As apparent from the results of Table-2, with the system using the ink of the invention, all the performances are excellent. Particularly, as compared with Comparative Examples, the image fastness property and the ink stability are excellent.

Example 4

The same ink as that manufactured in Example 3 was printed on the photo gloss paper "Gasai" manufactured by Fuji Photo Film Co., Ltd., by the same machine as that in Example 3. Then, the same evaluation as those in Example 3 were carried out. As a result, the same results were obtained.

Example 5

(Manufacturing of Ink Solution D)

2.5 g of the coloring matter of the invention (DYE-19) and 7.04 g of sodium dioctylsulfosuccinate were dissolved in 4.22 g of the following high boiling point organic solvent (s-2), 5.63 g of the following high boiling point organic solvent (s-11), and 50 ml of ethyl acetate at 70° C. To the resulting solution, 500 ml of deionized water was added with stirring by means of a magnetic stirrer. Thus, an oil-in-water type coarse particle dispersion was manufactured. Then, the coarse particle dispersion was allowed to pass through a Microfluidizer (MICROFLUIDEX INC) under a pressure of 600 bar five times to be finely reduced in size of particles. Further, the resulting emulsion was subjected to desolvation by means of a rotary evaporator until there was no odor of ethyl acetate. To the microfine emulsion of a hydrophobic dye thus obtained, 140 g of diethylene glycol, 50 g of glycerin, 7 g of SURFYNOL 465 (AirProducts & Chemical Co.), and 900 ml of deionized water were added to manufacture an ink solution D. The ink had a pH of 8.5, a viscosity of 4.1 mPa·S, and a surface tension of 33 mN/m.

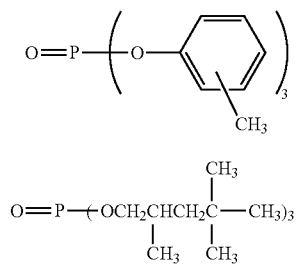

S-2

S-11

(Manufacturing of Ink Solution 103)

An ink solution 103 was manufactured in the same manner as with the ink solution D, except that the coloring matter of the invention of the ink solution D was changed to the equimolar comparative coloring matter of Table 3 below. The pH, viscosity, and surface tension of the ink solution were the same as those of the ink solution D.

(Image Recording and Evaluation)

For the ink solution D and the comparative ink solution 103, the following evaluations were carried out. The results are shown in Table 3 below.

Incidentally, in Table 3, the contents of "tone ($\lambda$max)", "light resistance", "ozone (gas) resistance", "heat resistance", and "ink stability" are respectively the same as those described in Example 3.

TABLE 3

| Sample | Coloring matter | Tone ($\lambda$max) | Light resistance | Ozone resistance | Heat resistance | Ink stability |
|---|---|---|---|---|---|---|
| D | DYE-19 | A | A | A | A | A |
| 103 | Comparative coloring matter C | B (430 nm) | C | C | A | A |

Comparative Coloring Matter c

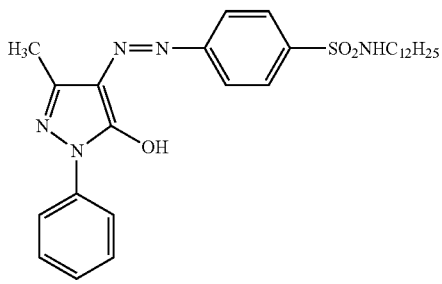

Apparent from Table 3, the ink for ink jet of the invention is excellent in tone, and excellent in light resistance, ozone resistance, heat resistance, and ink stability.

Example 6

The same ink as that manufactured in Example 5 was printed on the ink jet paper photo gloss paper "Gasai" manufactured by Fuji Photo Film Co., Ltd., by the same machine as that in Example 5. Then, the same evaluations as those in Example 5 were carried out. As a result, the same results as those in Example 5 were obtained.

Example 7

3 parts by mass of the coloring matter of the invention (DYE-20) and 100 parts by mass of a resin for toner [styrene-acrylic acid ester copolymer; trade name HIMER TB-1000F (manufactured by Sanyo Chemical Industries, Ltd.)] were mixed and ground in a ball mill. Then, the mixture was heated to 150° C. to be molten and mixed. After cooling, the mixture was coarsely crushed using a hammer mill, and then, finely pulverized by a pulverizer of an air jet system. The resulting particles were further classified, and 1 to 20 micro was selected, resulting in a toner. To 10 parts of the toner, 900 parts by mass of carrier iron powder (trade name EFV250/400; manufactured by Nippon Iron Powder) was uniformly mixed, resulting in a developer. Similarly, each sample was prepared in the same manner, except that the coloring matter shown in Table 4 was used in an amount of 3 parts by mass. By the use of these developers, copying was carried out by means of a dry ordinary paper electrophotographic copier [trade name NP-5000; manufactured by CANON, Corp.].

Reflected images (images on paper) and transmitted images (OHP images) were formed on paper and OHP sheets, respectively, with a developer using the color toner of the invention in accordance with the foregoing image forming method, and the evaluation tests were conducted in the following manner. Incidentally, the amount of the toner deposited was evaluated in the range of 0.7±0.05 (mg/cm$^2$).

The resulting images were evaluated for the hue and the light fastness property. The hue was visually rated on a scale of three levels of best, good, and bad. The evaluation results are shown in Table 4. In Table 4 below, AA denotes that the hue is best; BB denotes that the hue is good; and CC denotes that the hue is bad. The light fastness property was evaluated in the following manner. The image density Ci immediately after recording was measured, and thereafter, the image was irradiated with xenon light (85,000 lux) by means of a weather meter (Atlas C. 165), for 5 days. Then, the image density Cf was measured again, and the coloring matter residual ratio ({Ci−Cf/Ci}×100%) was calculated from the difference in image density between before and after xenon light irradiation. The image density was measured by means of a reflection densitometer (X-Rite 310TR). The evaluation results are shown in Table 4 below. In Table 4, the case where the coloring matter residual ratio was 90% or more is indicated with AA; the case of 90 to 80%, BB; and the case of less than 80%, CC.

The transparency of the OHP image was evaluated in the following manner. By means of a "330 model autographic spectrophotometer" manufactured by Hitachi Ltd., the visible spectral transmittance of the image was measured with the OHP sheet having no toner carried thereon as a reference. The spectral transmittance at 650 nm was determined, and taken as the scale for the transparency of the OHP sheet. The case of the spectral transmittance of 80% or more is indicated with AA; 70 to 80%, BB; and less than 70%, CC. The results up to this point are shown in Table 4.

TABLE 4

| | DYE-No. | Hue | Light fastness property | Transparency |
|---|---|---|---|---|
| Invention | DYE-20 | AA | AA | AA |
| Comparative Example | C.I. Solvent. Yellow 162 | BB | BB | BB |

Apparent from Table 4, use of the color toner of the invention provides faithful color reproduction and high OHP quality. For this reason, the color toner of the invention is suitable for use as a full color toner. Further, it is good in light resistance, which can provide images storable over a long period.

Example 8

<Formation of Heat Transfer Coloring Matter Donating Material>

As a support, a polyethylene terephthalate film subjected to a heat resistant slip treatment on the back side, and with a thickness of 6 μm (manufactured by TEIJIN Limited.) was used. Thus, on the surface of the film, a coating composition for a heat transfer coloring matter donating layer with the following composition was coated by means of wire bar coating and formed so that the thickness upon drying was 1.5 μm. Thus, a heat transfer coloring matter donating material (5-1) was formed.

Coating Composition for Heat Transfer Coloring Matter Donating Layer:

| | |
|---|---|
| Coloring matter (DYE-20) | 10 millimol |
| Polyvinyl butyral resin (Denka Butyral 5000-A manufactured by Denki Kagaku) | 3 g |
| Toluene | 40 ml |
| Methyl ethyl ketone | 40 ml |
| Polyisocyanate (Takenate D110N manufactured by Takeda Pharmaceutical Company Limited.) | 0.2 ml |

Then, a heat transfer coloring matter donating material of the invention and a heat transfer coloring matter donating material for comparison (5-2) were formed in the same manner as described above, except that the coloring matter (DYE-20) was changed to the comparative coloring matter described in Table 5.

(Formation of Heat Transfer Image Receiving Material>

As a support, a synthetic paper sheet with a thickness of 150 μm (YUPO-FPG150, manufactured by Oji Yuka) was used. Thus, on the surface, the following composition was coated by means of wire bar coating so that the thickness upon drying was 8 μm. Thus, a heat transfer image receiving material was formed. Drying was carried out in an oven at a temperature of 100° C. for 30 minutes after temporary drying by a dryer.

Coating Composition of Image Receiving Layer:

| | |
|---|---|
| Polyester resin (VYLON-280 manufactured by Toyobo Co., Ltd.) | 22 g |
| Polyisocyanate (KP-90 manufactured by Dainippon Ink & Chemicals, Inc.) | 4 g |
| Amino-modified silicone oil (KF-857 manufactured by Shin-Etsu Silicone) | 0.5 g |
| Methyl ethyl ketone | 85 ml |
| Toluene | 85 ml |
| Cyclohexanone | 15 ml |

The heat transfer coloring matter donating materials (5-1) and (5-2) and the heat transfer image receiving material obtained in the foregoing manner were stacked one on another in such a manner that the heat transfer coloring matter donating layers and the image receiving layer were in contact with one another. Printing was carried out using a thermal head from the support side of the heat transfer coloring matter donating material under conditions of a thermal head output of 0.25 W/dot, a pulse width of 0.15 to 15 msec, and a dot density of 6 dots/mm. Thus, a coloring matter of yellow was dyed in the form of an image in the image receiving layer of the image receiving material. The maximum color optical density of each resulting image is shown in Table 5. With the heat transfer coloring matter donating material (5-1) of the invention, it was possible to obtain clear image recording with no transfer blur. Then, each pre-recorded heat transfer image receiving material obtained in the foregoing manner was irradiated with a Xe light (17,000 lux) for 5 days to examine the light stability of the colored image. The status A reflection density after irradiation of the portion indicating a status A reflection density of 1.0 was measured. The stability was evaluated in terms of the residual ratio (percentage) relative to the reflection density of 1.0 before irradiation. The results are shown in Table 5.

TABLE 5

| Heat transfer coloring matter donating material | DYE-No. | Maximum density | Light fastness property | Remark |
|---|---|---|---|---|
| 5-1 | DYE-20 | 1.9 | 95 | Invention |
| 5-2 | Comparative coloring matter d | 1.8 | 52 | Comparative |

Comparative Coloring Matter d

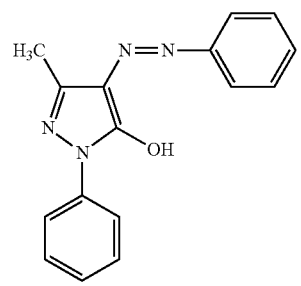 [SMILES: Cc1nn(-c2ccccc2)c(O)c1N=Nc1ccccc1]

As described above, the coloring matter of the invention was excellent in light fastness property as compared with the comparative dye. Further, the hue was also vivid.

Example 9

The color filter was manufactured in the following manner. Onto a silicon wafer, a positive type resist composition containing a thermosetting resin, a quinonediazide compound, a crosslinking agent, a coloring matter, and a solvent was spin coated. The solvent was evaporated by heating, followed by exposure to light through a mask, to decompose the quinonediazide compound. If required, after heating, development was carried out to obtain a mosaic pattern. The exposure to light was carried out by means of an i-ray exposure stepper HITACHI LD-5010-i (NA=0.40) manufactured by Hitachi Ltd. Whereas, the developer used was SOPD or SOPD-B manufactured by Sumitomo Chemical Co., Ltd.

<Preparation of Positive Type Resist Composition>

3.4 parts by mass of a cresol novolak resin (polystyrene equivalent molecular weight 4300) resulting from a m-cresol/p-cresol/formaldehyde (reaction mole ratio=5/5/7.5) mixture, 1.8 parts by mass of o-naphthoquinonediazide-5-sulfonic acid ester (an average of two hydroxyl groups have been esterified) manufactured by using a phenol compound represented by the following formula, 0.8 part by mass of hexamethoxymethylolated melamine, 20 parts by mass of ethyl lactate, and 1 part by mass of the coloring matter of the invention (DYE-20) shown in Table 6 were mixed, resulting in a positive type resist composition.

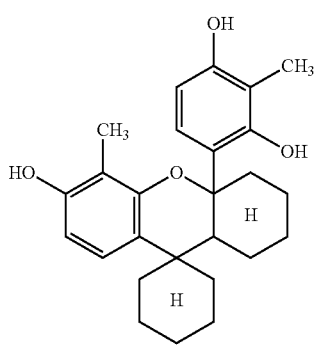

<Preparation of Color Filter>

The resulting positive type resist composition was spin coated onto a silicon wafer. Then, the solvent was evaporated. The silicon wafer was exposed to light, and then heated at 100° C. Then, the exposed portion was removed by the alkali development to obtain a positive type colored pattern having a 0.8-μm resolution. This was entirely exposed to light, and then, heated at 150° C. for 15 minutes, resulting in a cyan complementary color type color filter.

Comparative Example

In place of the yellow coloring matter of the invention used in the examples, 1 part by mass of Oleosol yellow 2G manufactured by Sumitomo Chemical Co., Ltd., was mixed, resulting in a positive type resist composition. The resulting positive type resist composition was spin coated onto a silicon wafer. Then, the solvent was evaporated. The silicon wafer was exposed to light, and then subjected to alkali development, resulting in a positive type colored pattern having a 1-μm resolution. This was entirely exposed to light, and then, heated at 150° C. for 10 minutes, resulting in a yellow color filter.

<Evaluation>

The transmission spectrum of the resulting yellow color filter was measured, and the cutting on the short wavelength side or the long wavelength side of the spectrum important for color reproduction was relatively evaluated. AA denotes good; BB denotes somewhat acceptable level; and CC, unacceptable level. Further, the filter was irradiated with xenon light (85000 1x) by means of a weather meter (Atlas C. 165) for 7 days. Then, the image densities before and after xenon irradiation were measured, and evaluation was carried out based on the coloring matter residual ratio.

TABLE 6

| | Dye-No. | Absorption characteristics | Light fastness property |
|---|---|---|---|
| Invention | DYE-20 | AA | 98% |
| Comparative Example | Oleosol yellow 2G | BB | 59% |

The coloring matter of the invention exhibits a sharper cutting on the short wavelength side or on the long wavelength side of the spectrum, and is excellent in color reproducibility as compared with Comparative Example. Further, it has been shown that the coloring matter of the invention is superior in light fastness property to the comparative compound.

INDUSTRIAL APPLICABILITY

The coloring matters of the invention are preferably used for various coloring compositions in ink for printing of ink jet or the like, an ink sheet in a heat sensitive recording material, a color toner for electrophotography, displays such as LCD and PDP, image pick-up devices such as CCDs, and dying solutions for dying of various fibers.

Although the invention has been described in detail, and with reference to specific embodiments thereof, it will be apparent to those skilled in the art that various changes and modifications can be made without departing from the spirit and the scope of the invention.

This application is based on Japanese Patent Application (Japanese Patent Application No. 2005-030466) filed on Feb. 7, 2005, and Japanese Patent Application (Japanese Patent Application No. 2005-226768) filed on Aug. 4, 2005, the contents of which are incorporated herein by reference.

The invention claimed is:

1. A compound represented by the following formula (7), or a salt or a hydrate thereof:

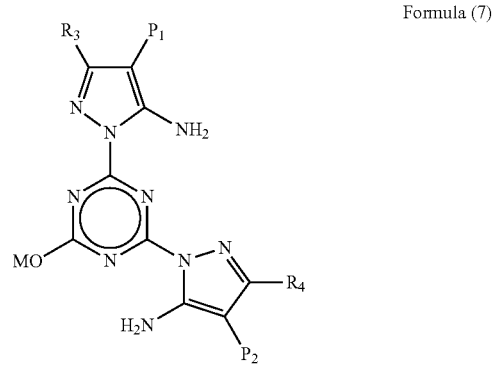

Formula (7)

wherein in the formula, $R_3$ and $R_4$ each independently represents a monovalent group; $P_1$ and $P_2$ each independently represents a hydrogen atom an alkyloxy group, an aryloxy group, an alkylthio group or an arylthio group; and M represents a hydrogen atom or a cation.

2. The compound according to claim 1, wherein $P_1$ and $P_2$ are a hydrogen atom.

* * * * *